United States Patent [19]

Peet et al.

[11] Patent Number: 5,698,523
[45] Date of Patent: Dec. 16, 1997

[54] ACYLATED ENOL DERIVATIVES AS PRODRUGS OF ELASTASE INHIBITORS

[75] Inventors: Norton P. Peet, Cincinnati; Joseph P. Burkhart; Shujaath Mehdi, both of West Chester, all of Ohio

[73] Assignee: Merrell Pharmaceuticals Inc., Cincinnati, Ohio

[21] Appl. No.: 670,136

[22] Filed: Jun. 25, 1996

Related U.S. Application Data

[63] Continuation of Ser. No. 420,859, Apr. 19, 1995, abandoned, which is a continuation-in-part of Ser. No. 252,798, Jun. 2, 1994, abandoned.

[51] Int. Cl.$^6$ .................. C07D 43/12; C07K 5/083; A61K 38/06
[52] U.S. Cl. .................. 514/18; 514/19; 514/237.2; 514/423; 548/537; 560/250; 560/253; 544/141; 530/330; 530/331
[58] Field of Search .................. 530/330, 331; 514/18, 19, 237.2, 423; 548/537; 560/250, 253; 544/141

[56] References Cited

U.S. PATENT DOCUMENTS

| | | | |
|---|---|---|---|
| 4,277,395 | 7/1981 | Bey et al. | 260/112.5 |
| 4,518,528 | 5/1985 | Rasnick | 260/112.5 |
| 4,623,639 | 11/1986 | Hassall | 514/18 |
| 4,629,724 | 12/1986 | Ryone et al. | 514/18 |
| 4,636,489 | 1/1987 | Seemuller et al. | 514/12 |
| 4,643,991 | 2/1987 | Digenis et al. | 514/18 |
| 4,855,303 | 8/1989 | Hoover | 514/18 |
| 4,873,221 | 10/1989 | Trainor et al. | 514/18 |
| 4,880,780 | 11/1989 | Trainor et al. | 514/18 |
| 4,910,190 | 3/1990 | Bergeson et al. | 514/19 |
| 4,935,405 | 6/1990 | Hoover et al. | 514/19 |
| 5,055,450 | 10/1991 | Edwards et al. | 514/19 |
| 5,114,927 | 5/1992 | Schirlin | 514/18 |
| 5,162,307 | 11/1992 | Digenis et al. | 514/19 |
| 5,221,665 | 6/1993 | Skiles | 514/18 |
| 5,478,811 | 12/1995 | Peet et al. | 514/17 |
| 5,496,927 | 3/1996 | Kolb et al. | 530/328 |
| 5,510,333 | 4/1996 | Angelastro et al. | 514/18 |

FOREIGN PATENT DOCUMENTS

| | | |
|---|---|---|
| 0009384 | 4/1980 | European Pat. Off. . |
| 0189305 | 7/1986 | European Pat. Off. . |
| 0195212 | 9/1986 | European Pat. Off. . |
| 0204571 | 12/1986 | European Pat. Off. . |
| 0318318 | 11/1988 | European Pat. Off. . |
| 0369391 | 5/1990 | European Pat. Off. . |
| 0410411 | 1/1991 | European Pat. Off. . |
| 0494071 | 1/1991 | European Pat. Off. . |
| 0529568 | 3/1993 | European Pat. Off. . |
| 9115487 | 3/1990 | WIPO . |
| 9113904 | 3/1991 | WIPO . |
| 9212140 | 7/1992 | WIPO . |
| 9215605 | 9/1992 | WIPO . |
| 9509838 | 4/1995 | WIPO . |
| 9533478 | 12/1995 | WIPO . |
| 9533762 | 12/1995 | WIPO . |
| 9533763 | 12/1995 | WIPO . |

OTHER PUBLICATIONS

Skiles et al., J. Med. Chem. 1992, 35, pp. 641–662, "Inhibition of Human Leukocyte Elastase (HLE) by N–Substituted Peptidyl Trifluoromethyl Ketones[1]".

Skiles et al., J. Med. Chem. 1992, 35, pp. 4795–4808, "Inhibition of Human Leukocyte Elastase by N–Substituted Peptides Containing alpha", alpha–Difluorostatone Residues at $P_1$.

Williams et al., publication, "Biologic Characterization of ICI 200,880 and ICI 200,355", Novel Inhibitors of Human Neutrophil Elastase 1,2 Am Rev. Respir. Dis. 1991, 144:875–883.

Kawase et al., Tetrahedron Letters, vol. 34, No. 5 pp. 859–862, 1993, "Unexpected Product from the Dakin–West Reaction of N–Acylprolines using Trifluoroacetic Anhydride: A Novel Access to 5–Trifluoromethyl–oxazoles".

Kawase, J. Chem. Soc., Chem. Commun., 1992, pp. 1076–1077, "Unusual Ring Expansion observed during the Dakin–West Reaction of Tetrahydroisoquinoline–1–carboxylic Acids using Trifluoroacetic Anhydride: an Expedient Synthesis of 3–Benzazepine Derivatives bearing a Trifluoromethyl Group".

Imperiali et al., "Inhibition of Serine Proteases by Peptidyl Flourumethyl Ketones," Biochemistry vol. 25, pp. 3760–3767 month not available (1986).

Skiles et al., "Inhibition of Human Leukocyte Elastase (HLE) by N–Substituted Peptidyl Trifluoromethyl Ketones," J. of Medicinal Chemistry, vol. 35, No. 4, pp. 641–662 month not available (1992).

Repine et al., "Renin Inhibitors Containing Esters at the $P_2$–Position. Oral Activity in a Derivative of Methyl Aminomalonate," J. Med. Chem. 34, pp. 1935–1943, month not available (1991).

Ueda et al., "The synthesis of arginylfluoroalkanes, their inhibition of trypsin and blood–coagulation serine proteinases and their anticoagulant activity," Biochem. J. 265, pp. 539–545, (1990).

Sham, H.L. et al., "Highly potent and specific inhibitors of human renin," FEBS Letters, vol. 220, No. 2, pp. 299–301, Aug. (1987).

Chemical Abstract Vo. 111, No. 9, Aug. 28, 1989, Lafuma et al. 111:70314q.

Powers et al, Chemical Abstracts, vol. 108:33954r, month not available 1988, Mechanism–based inhibitors of human leukocyte elastase.

Steinmeyer et al, Influence of Some Natural and Semisynthetic Agents on Elastase and Cathepsin G from Polymorphonuclear Granulocytes, Arzneim–Forsch/Drug Res. 41(1), Nr. month not available (1991), pp. 77–80.

(List continued on next page.)

*Primary Examiner*—José G. Dees
*Assistant Examiner*—Laura L. Stockton
*Attorney, Agent, or Firm*—William R. Boudreaux

[57] ABSTRACT

This invention relates to acylated enol derivatives of known elastase inhibitors. These compounds are useful in the treatment of various inflammatory diseases, including cystic fibrosis and emphysema or as prodrugs of compounds which are useful in the treatment of said diseases.

24 Claims, 2 Drawing Sheets

OTHER PUBLICATIONS

McWherter et al, Novel Inhibitors of Human Leukocyte Elastase and Cathepsin G, Sequence Variants of Squash Seet Protease Inhibitor with Altered Protease Selectivity, Biochemistry month not available, 1989, 28, 5708–5713.

Reilly et al., The Degradation of Human Lung Elastin by Neutrophil Proteinases, Biochimica et Biophysica Acta, 621 month not available (1980) pp. 147–157.

Nakajima et al, Mapping the Extended Substrate Binding Site of Cathepsin G and Human Luekoocyte Elastase, The Journal of Biological Chemistry vol 254, No. 10, pp. 4027–4032, May 1979.

Rice et al, Regulation of Proteolysis at the Neutrophil–Substrate Interface by Secretory Leukoprotease Inhibitor, Science, vol. 249, pp. 178–181, Jul. 1990.

Travis, Structure, Function, and control of Neutrophil Proteinases, Jun. 24, 1988, The American Journal of Medicine, vol. 84 (Suppl 6A) pp. 37–42.

Powers, J.C., Eleventh American Peptide Syposium, Abstracts, The Salk Institute and U. of CA, San Diego (1989). Internal notes taken at meeting.

Travis, J. et al., "Potential Problems in Designing Elastase Inhibitors for Therapy," Am Rev Respir Dis, Pulmonary Perspective, vol. 143 pp. 1412–1415 month not available 1991.

Petrillo, E.W., et al., Chapter 6. Antihypertensive Agents, Section II. Cardiovascular and Pulmonary Agents, Annual Reports in Medicinal Chemistry, 25, month not available 1989, Academic Press, Inc., D.W. Robertson Editor.

Chemical Abstract vol. 111, No. 21, Nov. 20, 1989, Galzigna et al. 111:190/312.

Angelastro et al, "An Efficient Synthesis of Novel a–Diketone and A–Keto Ester Derivatives of N–Protected Amino Acids and Peptides" *J. Org. Chem.* 54, pp. 3913–3916 month not available (1989).

Angelastro et al, "Inhibition of Human Neurtophil Elastase with Peptidyl Electrophilic Ketones. 2. Orally Active $P_G$–Val–Pro–Val–Pentafluoroethyl Ketones" *Journal of Medicinal Chemistry*, 37 month not available (1994).

Angelastro et al., "Janus Compounds: Dual Inhibitors of Proteinases" *Bioorganic & Medicinal Chemistry Letters*, vol. 3, No. 4, pp. 525–530 month not available (1993).

Mehdi, "Synthetic and Naturally Occurring Protease Inhibitors Containing an Electrophilic Carbonyl Group." *Bioorganic Chemistry*, 21, pp. 249–259 month not available (1993).

Angelastro et al., "Efficient Preparation of Peptidyl Pentafluoroethyl Ketones" *Tetrahedron Letters*, vol. 33, No. 23, pp. 3265–3268 month not available (1992).

Burkhart, et al, "A Novel Method for the Preparation of Peptidyl a–Keto Esters" *Tetrahedron Letters*, vol. 31, No. 10, pp. 1385–1388 month not available (1990).

Peet et al, Synthesis of Peptidyl Fuuoromethyl Ketones and Peptidyl α–Keto Esters as Inhibitors of Procine Pancreatic Elastase, Human Neutrophil Elastase, and Rat and Human Neutrophil Cathepsin G,J. Med Chem, month not available 1990, 33, pp. 394–407.

Doherty et al, Novel Inhibitors of Polymorphonuclear Neutrophil (PMN) Elastase and Cathepsin G: Evaluation in vitro of their potential for the Treatment of inflammatory connective tissue damage, Int. J. Immunopharmac, vol. 12, No. 7, pp. 787–795, month not available 1990.

Mehdi et al, The inhibition of human Neutrophil elastase and cathepsin G by Peptidyl 1,2–dicarbonyl derivatives, Biochemical and Biophysical Research Communications, vol. 166, No. 2, Jan. 1990, pp. 595–600.

Shah et al., Orally Active β–Lactam Inhibitors of Human Leukocyte Elastase–1. J. Med Chem, 35, pp. 3745–3754 month not available (1992).

Snider, Experimental Studies on Emphysema and Chronic Bronchial Injury, Eur. J. Respir Dis month not available (1986) 69 (Suppl. 146) pp. 17–35.

Malech et al, Current Concepts: Immunology Neutrophils in Human Diseases, Medical Intelligence–vol. 317. No. 11, Sep. 1987.

Fletcher et al, A comparison of $\alpha_1$–Proteinase Inhibitor Methoxysuccinyl–ala–ala–pro–val–chloromethylketone and Specific β–Lactam Inhibitors in a accute Model of Human Polymorphonuclear Leukocyte Elastase–induced Lung Hemorrhage in the hamster, Am Rev Respir Dis month not available 990; 141:672–677.

Hassall et al, A new class of inhibitors of human leucocyte elastase, FEBS 2444, vol. 183, No. 2, Apr. 1985.

Bundgaard, Hans, "Design of Bioreversible Drug Derivatives and the Utility of the Double Prodrug Concept", *Bioreversible Carriers In Drug Design*, 1987 pp. 13, 63–65.

Imperiali et al, *Biochemistry*, vol. 21, pp. 3760–3767 (1986).

Powers, J.C., Eleventh American Peptide Symposium, Abstracts, The Salk Institute and U. of CA, San Diego (1989). Internal Notes taken at meeting.

Angelastro et al, *Bioorganic & Medicinal Chemistry Letters*, vol. 2, No 10, pp. 1235–1238 (1992).

J. Med. Chem. 33, pp. 11–13 (1990) "Communications to the Editor".

Copeland, T.D. et al, Biochem. Biophys. Res. Commun,. vol. 169., No. 1, pp. 310–314 (1990).

P.G. Gassman et al, J. Org. Chem. vol. 52, pp. 2481–2490, (1987).

Desai, R.C. et al, Bioorg. Med. Chem. Lett. 5, pp. 105–109 (1995).

Davies, P., et al Ann. N.Y. Acad. Sci. 624, pp. 219–233 (1992).

Durham et al, J. Pharm. Exp. Ther., vol. 270, No. 1, pp. 185–191 (1994).

Zhaozhao Li et al, J. Med. Chem, 1993, 36, pp. 3472–3480.

Isabel Charles et al, J.C.S. Perkin I, 1980, pp. 1139–1146.

Janusz, M. et al, J. Immunol. (1991), vol. 146, pp. 3922–3928.

Janusz, M. et al, J. Pharmacol. Exp. Ther., (1995), vol. 275, pp. 1233–1238.

Burkhart et al, J. Med. Chem., 38, pp. 223–233 (1995).

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Xaa Xaa Xaa Xaa
    1

( 2 ) INFORMATION FOR SEQ ID NO:2:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="tert-butyloxycarbonyl protected"

( i x ) FEATURE:
        ( A ) NAME/KEY: Modified-site
        ( B ) LOCATION: 3
        ( D ) OTHER INFORMATION: /note="Terminal OH is replaced by modified valine analog"

( x i ) SEQUENCE DESCRIPTION: SEQ ID NO:2:

Xaa Ala Xaa
    1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Xaa Xaa Xaa Xaa
    1

( 2 ) INFORMATION FOR SEQ ID NO:4:

( i ) SEQUENCE CHARACTERISTICS:
        ( A ) LENGTH: 4 amino acids
        ( B ) TYPE: amino acid (D) TOPOLOGY: linear (ii) MOLECULE TYPE: peptide (xi) SEQUENCE DESCRIPTION: SEQ ID NO:4:

Xaa Xaa Xaa Xaa
1

(2) INFORMATION FOR SEQ ID NO:5:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:5:

Xaa Xaa Xaa Xaa
1

(2) INFORMATION FOR SEQ ID NO:6:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:6:

Xaa Xaa Xaa Xaa
1

(2) INFORMATION FOR SEQ ID NO:7:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:7:

Xaa Xaa Xaa Xaa
1

(2) INFORMATION FOR SEQ ID NO:8:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:8:

Xaa Xaa Xaa Xaa
1

(2) INFORMATION FOR SEQ ID NO:9:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:9:

Xaa Xaa Xaa Xaa
    1

( 2 ) INFORMATION FOR SEQ ID NO:10:

( i ) SEQUENCE CHARACTERISTICS:
          ( A ) LENGTH: 4 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:10:

Xaa Xaa Xaa Xaa
    1

( 2 ) INFORMATION FOR SEQ ID NO:11:

( i ) SEQUENCE CHARACTERISTICS:
          ( A ) LENGTH: 4 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:11:

Xaa Xaa Xaa Xaa
    1

( 2 ) INFORMATION FOR SEQ ID NO:12:

( i ) SEQUENCE CHARACTERISTICS:
          ( A ) LENGTH: 4 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:12:

Xaa Xaa Xaa Xaa
    1

( 2 ) INFORMATION FOR SEQ ID NO:13:

( i ) SEQUENCE CHARACTERISTICS:
          ( A ) LENGTH: 4 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:13:

Xaa Xaa Xaa Xaa
    1

( 2 ) INFORMATION FOR SEQ ID NO:14:

( i ) SEQUENCE CHARACTERISTICS:
          ( A ) LENGTH: 4 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:14:

Xaa Xaa Xaa Xaa
    1

( 2 ) INFORMATION FOR SEQ ID NO:15:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:15:

Xaa Xaa Xaa Xaa
1

ACYLATED ENOL DERIVATIVES AS PRODRUGS OF ELASTASE INHIBITORS

This is a continuation, of application Ser. No. 08/420,859, filed Apr. 19, 1995, now abandoned, which is a continuation in part of Ser. No. 08/252,798, filed Jun. 2, 1994, now abandoned, which is herein incorporated by reference.

BACKGROUND OF THE INVENTION

This invention relates to compounds which are either elastase inhibitors or are prodrugs of elastase inhibitors, useful for a variety of physiological and end-use applications.

Human neutrophil elastase has been implicated as an agent contributing to the tissue destruction associated with a number of inflammatory diseases such as chronic bronchitis, cystic fibrosis, and rheumatoid arthritis. J. L. Malech and J. I. Gallin, New Engl. J. Med., 317(11), 687 (1987). Elastase possesses a broad range of proteolytic activity against a number of connective tissue macromolecules including elastin, fibronectin, collagen, and proteoglycan. The presence of the enzyme elastase may contribute to the pathology of these diseases.

Normal plasma contains large quantities of protease inhibitors that control a variety of enzymes involved in connective tissue turnover and inflammation. For example, α-1-proteinase inhibitor (α-1-PI) is a serine protease inhibitor that blocks the activity of elastase. α-1-PI has received considerable interest because reduction in plasma levels to less than 15% of normal is associated with the early development of emphysema.

In addition to plasma derived protease inhibitors, secretory fluids, including bronchial, nasal, cervical mucus, and seminal fluid contain an endogenous protease inhibitor called secretory leukoprotease inhibitor (SLPI) that can inactivate elastase and is believed to play an important role in maintaining the integrity of the epithelium in the presence of inflammatory cell proteases. In certain pathological states α-1-PI and SLPI are inactivated by neutrophil oxidative mechanisms allowing the neutrophil proteases to function in an essentially inhibitor-free environment. For example, bronchial lavage fluids from patients with adult respiratory distress syndrome (ARDS) have been found to contain active elastase and α-1-PI that had been inactivated by oxidation.

In addition to oxidative mechanisms, neutrophils possess non-oxidative mechanisms for eluding inhibition by antiproteases. Neutrophils from patients with chronic granulomatous disease are capable of degrading endothelial cell matrices in the presence of excess α-1-PI. There is considerable in vitro evidence that stimulated neutrophils can tightly bind to their substrates such that serum antiproteases are effectively excluded from the microenvironment of tight cell-substrate contact. The influx of large numbers of neutrophils to an inflammatory site may result in considerable tissue damage due to the proteolysis that occurs in this region.

Applicants have determined that elastase is one of the primary neutrophil proteases responsible for cartilage matrix degeneration as measured by the ability of neutrophil lysate, purified elastase and stimulated neutrophils to degrade cartilage matrix proteoglycan. Furthermore, applicants have previously discovered peptide derivatives useful as elastase inhibitors, exerting valuable pharmacological activities. For example, peptide derivatives useful as elastase inhibitors wherein the carboxy terminal carboxyl group has been replaced by a pentafluoroethylcarbonyl (—C(O)C$_2$F$_5$) group and in which the amino terminal amino acid is protected by various heterocycle-containing groups such as a 4-morpholinecarbonyl group are disclosed in European Patent Application OPI No. 0529568, inventors Peet et al., with a publication date of Mar. 3, 1993. Applicants have recently discovered acylated enol derivatives of known elastase inhibitors, such as those disclosed in European Patent Application OPI No. 0529568, which are useful as prodrugs of the known derivatives, or are elastase inhibitors in their own right.

SUMMARY OF THE INVENTION

The present invention relates to compounds having the following formula 1

K-P$_4$-P$_3$-P$_2$-EAC            1 (SEQ. ID NO. 1)

wherein
EAC is a group of the formulae $$\text{\textit{(structure with } CFR_3R_4, H, N, R_1, O, C, R_2\text{)}}$$

or $$\text{\textit{(structure with } H, N, R_1, O, C, R_2, CFR_3R_4\text{)}}$$

wherein

R$_1$ is —CH$_3$, —CH(CH$_3$)$_2$, —CH$_2$CH$_2$CH$_3$, —CH$_2$CH(CH$_3$)$_2$ or —CH(CH$_3$)CH$_2$CH$_3$;

R$_2$ is —H, or is a (C$_{1-8}$)alkyl, (C$_{3-12}$)cycloalkyl, (C$_{6-10}$)aryl or (C$_{6-10}$)aryl(C$_{1-6}$)alkyl;

R$_3$ is —H or —F;

R$_4$ is —H, —F, —CF$_3$, —CF$_2$CF$_3$, —CF$_2$CF$_2$CF$_3$, —C(O)OR$_5$, or —C(O)NR$_5$R$_6$ or is a (C$_{1-8}$)alkyl, (C$_{3-12}$)cycloalkyl, (C$_{6-10}$)aryl or (C$_{6-10}$)aryl(C$_{1-6}$)alkyl;

R$_5$ and R$_6$ are each independently —H, or a (C$_{1-8}$)alkyl, (C$_{3-12}$)cycloalkyl, (C$_{6-10}$)aryl or (C$_{6-10}$)aryl(C$_{1-6}$)alkyl;

P$_2$ is Ala, bAla, Leu, Ile, Val, Nva, bVal, Met, Nle, Gly Phe, Tyr, Trp, or Nal(1) where the nitrogen of the alpha-amino group can be substituted with an R group where R is a (C$_{1-8}$)alkyl, (C$_{3-12}$)cycloalkyl, (C$_{3-12}$) cycloalkyl(C$_{1-6}$)alkyl, (C$_{4-11}$)bicycloalkyl, (C$_{4-11}$) bicycloalkyl(C$_{1-6}$)alkyl, (C$_{6-10}$)aryl, (C$_{6-10}$)aryl(C$_{1-6}$) alkyl, (C$_{3-7}$)heterocycloalkyl, (C$_{3-7}$)heterocycloalkyl (C$_{1-6}$)alkyl, (C$_{5-9}$)heteroaryl, (C$_{5-9}$)heteroaryl(C$_{1-6}$) alkyl, fused (C$_{6-10}$)aryl-(C$_{3-12}$)cycloalkyl, fused (C$_{6-10}$) aryl(C$_{3-12}$)cyclo-alkyl(C$_{1-6}$)alkyl, fused (C$_{5-9}$) heteroaryl(C$_{3-8}$)cyclo-alkyl, or fused (C$_{5-9}$)heteroaryl (C$_{3-12}$)cycloalkyl-(C$_{1-6}$)alkyl or P$_2$ is Pro, Ind, Tic, Pip, Tca, Pro(4-OBzl), Aze, Pro(4-OAc), Pro(4-OH);

P$_3$ is Ala, bAla, Leu, Ile, Val, Nva, bVal, Met, or Nle or an N-methyl derivative, Pro, Ind, Tic or Tca, or Lys substituted on its epsilon amino group with a morpholino-B-group or Orn substituted on its delta amino group with a morpholino-B-group;

P$_4$ is Ala, bAla, Leu, Ile, Val, Nva, bVal, Met, or Nle or a bond;

K is hydrogen, formyl, acetyl, succinyl, benzoyl, t-butyloxycarbonyl, carbobenzyloxy, tosyl, dansyl, isovaleryl, methoxysuccinyl, 1-adamantanesulphonyl, 1-adamantaneacetyl, 2-carboxybenzoyl, phenylacetyl, t-butylacetyl, bis((1-naphthyl)methyl)acetyl, —C(O)N—(CH$_3$)$_2$,

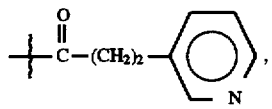

-A-R$_z$ wherein

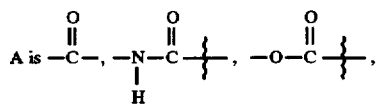

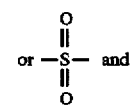

R$_z$ is an aryl group containing 6, 10 or 12 carbons suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino wherein the alkyl group contains 1 to 6 carbons, 5-tetrazolyl, and acylsulfonamido containing from 1 to 15 carbons, provided that when the acylsulfonamido contains an aryl the aryl may be further substituted by a member selected from fluoro, chloro, bromo, iodo and nitro; and such other terminal amino protecting groups which are functionally equivalent thereto, or

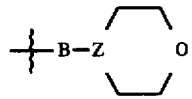

wherein
Z is N or CH, and
B is a group of the formulae

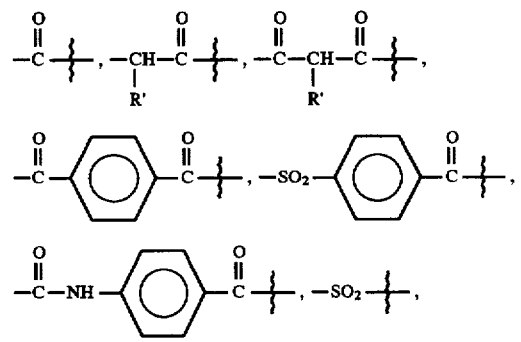

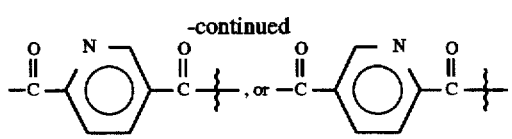

(the wavy line ∫ being the attachment to the rest of the molecule, i.e., not to Z) and wherein R' is hydrogen or a C$_{1-6}$alkyl group; or a hydrate, isostere or pharmaceutically acceptable salt thereof, useful as prodrugs of known elastase inhibitors or inhibit elastase in their present form. The compounds of formula 1 thus either exhibit an anti-inflammatory effect useful in the treatment of emphysema, cystic fibrosis, adult respiratory distress syndrome, septicemia, disseminated intravascular coagulation, gout, rheumatoid arthritis, chronic bronchitis and inflammatory bowel disease; or are prodrugs of compounds which exhibit such effects.

1 elastase+elastase substrate
2 elastase+elastase substrate+esterase
3 elastase+elastase substrate+MDL 103,279
4 elastase+elastase substrate+esterase+MDL 103,279

Figure 1:
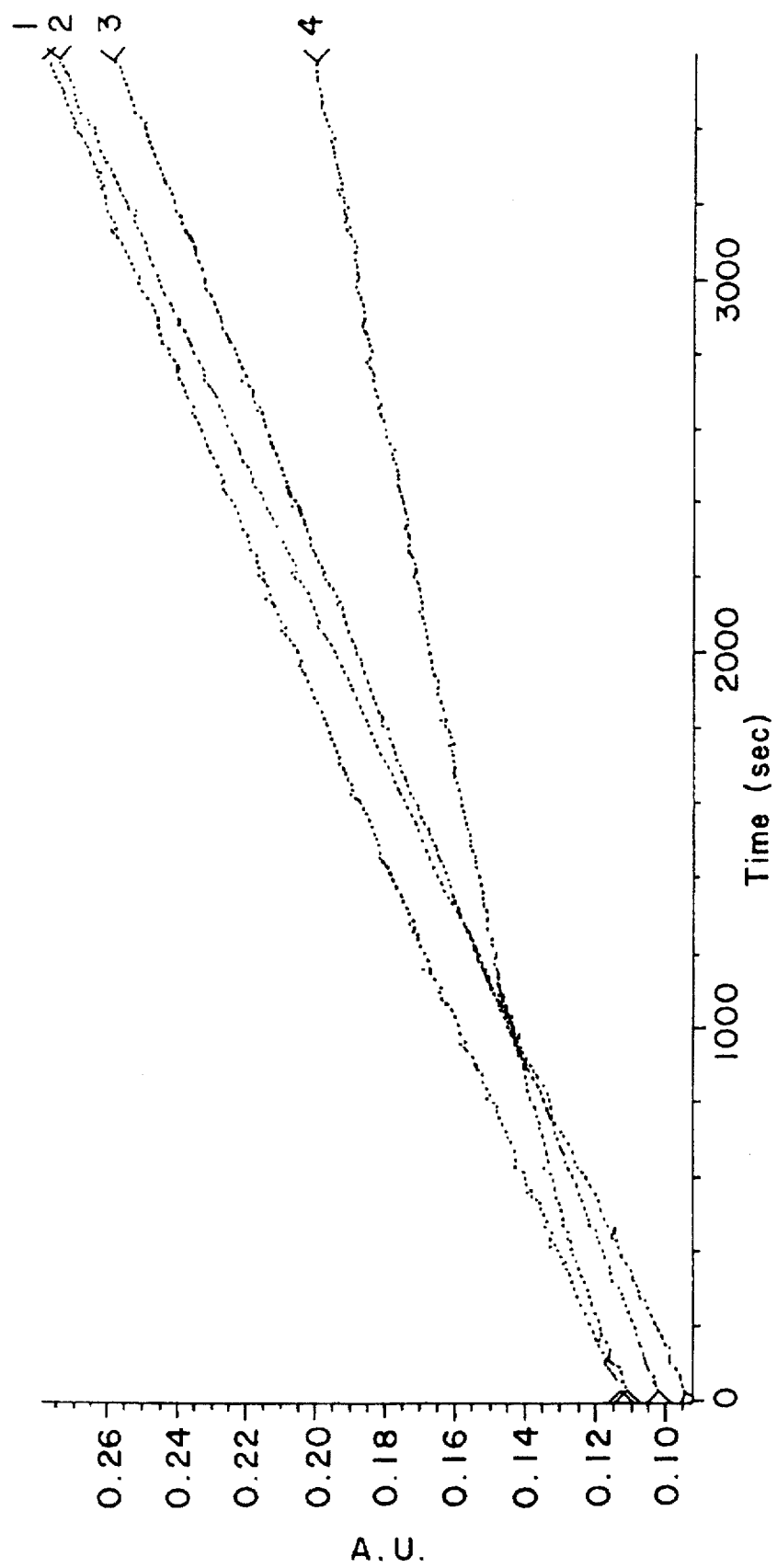
FIG. 1 illustrates the comparison of time courses of the assay of human neutrophil elastase as described in Example 9, disclosed herein, using MDL 103,279, over a 60 minute time frame with various controls. The abscissa (x-axis) represents the absorbance due to the formation of the product of the elastase reaction. The ordinate (y-axis) indicates the elapsed time of reaction measured in seconds. The increase in absorbance with time represents the rate of the elastase reaction. Identity of each time course line is as listed below.
Figure 2:
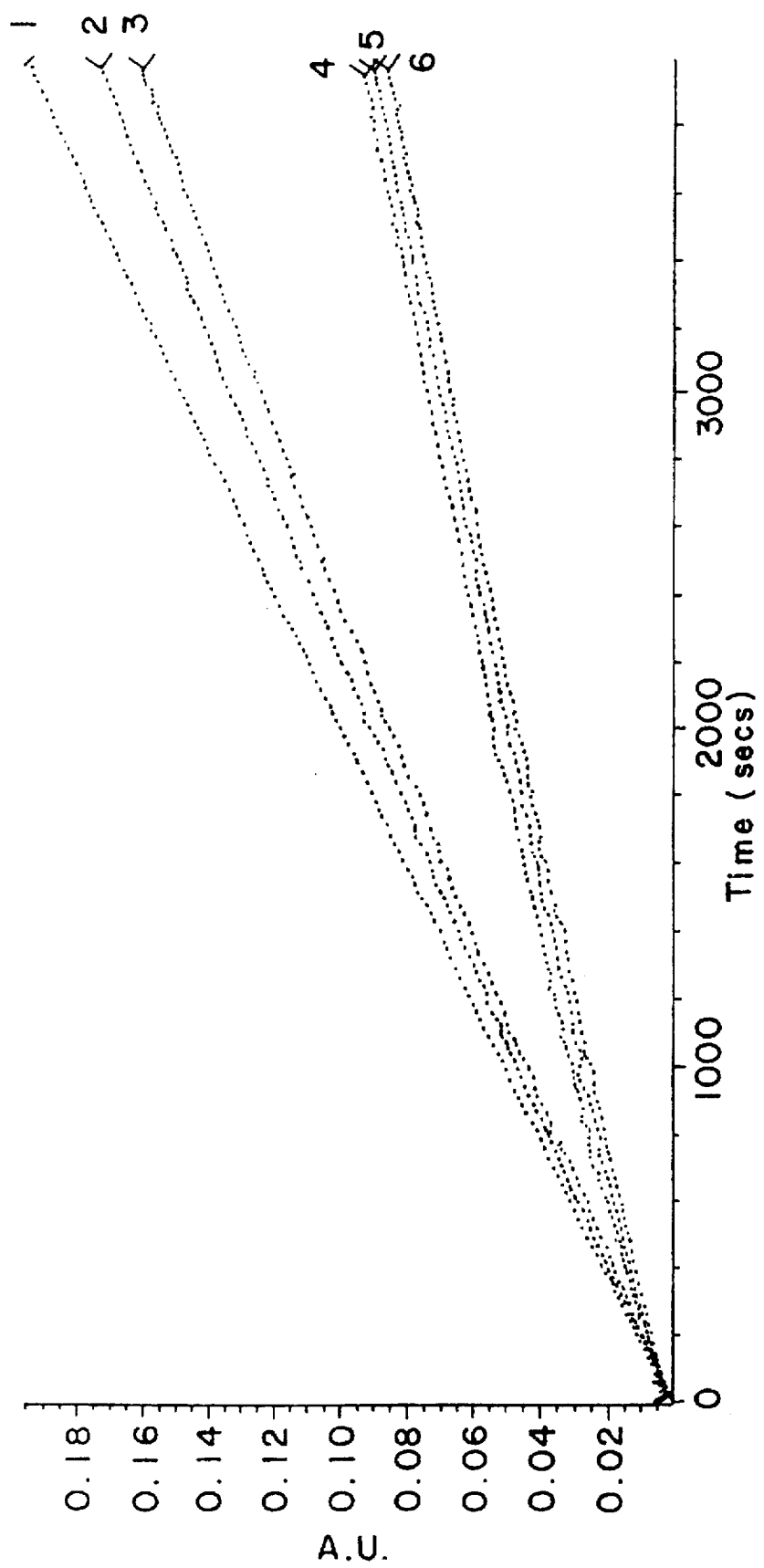

FIG. 2 illustrates the comparison of time courses of MDL 105,457, MDL 104,226, MDL 105,658, control and control+ esterase with MDL 103,279 using the assay of human neutrophil elastase as described in Example 9, disclosed herein. The abscissa and ordinate are defined the same as they are in FIG. 1. Identity of each time course line is as listed below.

1 control
2 control+esterase
3 66 nm MDL 105,457+esterase
4 66 nm MDL 103,279-02+esterase
5 66 nm MDL 104,226+esterase
6 66 nm MDL 105,658+esterase

DETAILED DESCRIPTION OF THE INVENTION

Isosteres of the compounds of formula 1 include those wherein (a) one or more of the α-amino residues of the P$_2$–P$_4$ substituents are in its unnatural configuration (when there is a natural configuration) or (b) when the normal peptidic amide linkage [—C(=O)NH—] is modified, such as for example, to form —CH$_2$NH— (reduced), —COCH$_2$— (keto), —CH(OH)CH$_2$— (hydroxy), —CH(NH$_2$)CH$_2$— (amino), —CH$_2$CH$_2$— (hydrocarbon), —CH=CH-(alkene). Preferably a compound of the invention should not be in an isosteric form; particularly it is preferred that there be no modified peptidic amide group, but if there is, it is preferable to keep the isosteric modifications to a minimum.

As used herein the term "(C$_{1-8}$)alkyl" means a straight or branched alkyl group of from 1 to 8 carbon atoms, such as, methyl, ethyl, n-propyl, isopropyl, n-butyl, n-pentyl, sec-pentyl, iso-pentyl, n-hexyl, heptyl and octyl. Similarly, the term "$(C_{1-6})$alkyl" means a straight or branched alkyl group of from 1 to 6 carbon atoms, such as, methyl, ethyl, n-propyl, isopropyl, n-butyl, n-pentyl, sec-pentyl, iso-pentyl and n-hexyl. The term "$(C_{3-12})$cycloalkyl" means a cyclic alkyl group consisting of a 3 to 12 member ring which can be substituted by a lower alkyl group, for example, cyclopropyl, cyclobutyl, cyclopentyl, cyclohexyl, 4-methylcyclohexyl, 4-ethylcyclohexyl, cycloheptyl, and cyclooctyl. The term "$(C_{3-12})$cycloalkyl$(C_{1-6})$alkyl" means a $(C_{1-6})$alkyl group substituted by a $(C_{3-12})$cycloalkyl group, such as a cyclohexylmethyl or cyclopentylethyl group. The term "$(C_{4-11})$bicycloalkyl" means an alkyl group containing one pair of bridgehead carbon atoms, such as 2-bicyclo[1.1.0]butyl, 2-bicyclo[2.2.1]hexyl, and 1-bicyclo[2.2.2]octane. The term "$(C_{4-11})$bicycloalkyl$(C_{1-6})$alkyl" means a $(C_{1-6})$alkyl substituted by a $(C_{4-11})$bicycloalkyl, such as 2-bicyclo-hexylmethyl. The term "$(C_{6-10})$aryl" means a cyclic, aromatic assemblage of conjugated carbon atoms, for example, phenyl, 1-naphthyl, and 2-naphthyl. The term "$(C_{6-10})$aryl$(C_{1-6})$alkyl" means a $(C_{1-6})$alkyl substituted by a $(C_{6-10})$aryl, such as benzyl, phenethyl, and 1-naphthylmethyl. The term "$(C_{3-7})$heterocycloalkyl" means a nonaromatic, carbon containing cyclic group which contains from 1 to 3 heteroatoms selected from oxygen, nitrogen and sulfur, such as morpholinyl and piperidinyl. The term "$(C_{3-7})$heterocycloalkyl$(C_{1-6})$alkyl" means a $(C_{1-6})$alkyl group substituted by a $(C_{3-7})$heterocycloalkyl group, for example, morpholinomethyl. The term "$(C_{5-9})$heteroaryl" means a cyclic or bicyclic, aromatic assemblage of conjugated carbon atoms and from 1 to 3 nitrogen, oxygen, and sulfur atoms, for example, pyridinyl, 2-quinoxalinyl, and quinolinyl. The term "$(C_{5-9})$heteroaryl$(C_{1-6})$alkyl" means $(C_{1-6})$alkyl group substituted by a $(C_{5-9})$heteroaryl group, such as, 3-quinolinylmethyl. The term "fused $(C_{6-10})$aryl $(C_{3-12})$cycloalkyl" means a "$(C_{3-12})$cycloalkyl" group which has one or more sides shared with a "$(C_{6-10})$aryl" group and can, for example, include groups derived by the fusion of benzene and cyclopentane, that is 2-indanyl. The term "fused $(C_{6-10})$aryl$(C_{3-12})$cycloalkyl$(C_{1-6})$alkyl" means a $(C_{1-6})$alkyl substituted by a fused $(C_{6-10})$aryl$(C_{3-12})$cycloalkyl group. The term "fused $(C_{5-9})$heteroaryl$(C_{3-8})$cycloalkyl" means a $(C_{5-9})$heteroaryl group which has one or more sides shared with a $(C_{3-8})$cycloalkyl group and can, for example, include groups derived by the fusion of cyclohexane and pyridine, that is tetrahydroquinoline. Finally the term "fused $(C_{5-9})$heteroaryl$(C_{3-8})$cycloalkyl$(C_{1-6})$alkyl" means a $(C_{1-6})$alkyl substituted by a fused $(C_{5-9})$heteroaryl$(C_{3-8})$cycloalkyl group.

Each α-amino acid has a characteristic "R-group", the R-group being the side chain, or residue, attached to the α-carbon atom of the α-amino acid. For example, the R-group side chain for glycine is hydrogen, for alanine it is methyl, for valine it is isopropyl. For the specific R-groups or side chains of the α-amino acids see A. L. Lehninger's text on Biochemistry.

Unless otherwise stated, the α-amino acids of these peptidase substrate analogs are preferably in their L-configuration; however, applicants contemplate that the amino acids of the formula 1 compounds can be of either the D- or L-configurations or can be mixtures of the D- and L-isomers, including the racemic mixture. The recognized abbreviations for the α-amino acids are set forth in Table I.

TABLE I

| AMINO ACID | SYMBOL |
|---|---|
| Alanine | Ala |
| Glycine | Gly |
| Isoleucine | Ile |
| Leucine | Leu |
| Lysine | Lys |
| Phenylalanine | Phe |
| Proline | Pro |
| Tryptophan | Trp |
| Tyrosine | Tyr |
| Valine | Val |
| Norvaline | Nva |
| Norleucine | Nle |
| 1-Naphthylalanine | Nal(1) |
| 2-Indolinecarboxylic acid | Ind |
| Sarcosine | Sar |
| beta-Alanine | bAla |
| beta-Valine | bVal |
| Methionine | Met |
| 1,2,3,4-Tetrahydro-3-isoquinoline carboxylic acid | Tic |
| Thiazolidine-4-carboxylic acid | Tca |
| Ornithine | Orn |
| Pipecolinic acid | Pip |
| Azetidine carboxylic acid | Aze |
| 4-Hydroxyproline | Pro(4-OH) |
| 4-Acetoxyproline | Pro(4-OAc) |
| 4-Benzyloxyproline | Pro(4-OBzl) |

Preferred embodiments of the subject compounds of the present invention are best realized in the compounds of formula 1 wherein:

$R_1$ is —$CH(CH_3)_2$ or —$CH_2CH_2CH_3$; preferably —$CH(CH_3)_2$;

$R_2$ is —H, $(C_{1-8})$alkyl, $(C_{3-12})$cycloalkyl or $(C_{6-10})$aryl; preferably —H, methyl, ethyl, n-propyl, isopropyl, n-butyl, cyclopentyl, cyclohexyl, cyclohexylmethyl, phenyl or benzyl;

$R_3$ is —F;

$R_4$ is —H, —F, —$CF_3$, —$C(O)OR_5$, —$C(O)NR_5R_6$, $(C_{1-8})$alkyl, cyclopentyl, cyclohexyl, phenyl or benzyl;

$R_5$ and $R_6$ are each independently —H, $(C_{1-8})$alkyl, cyclopentyl, cyclohexyl, phenyl, or benzyl;

$P_2$ is a Pro, Pip, Aze or Pro(4-OBzl);

$P_3$ is Ile, Val or Ala;

$P_4$ is Ala or a bond;

K is benzoyl, t-butyloxycarbonyl, carbobenzyloxy, isovaleryl, —$C(O)N(CH_3)_2$,

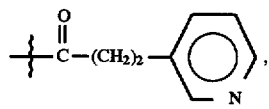

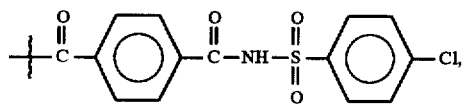

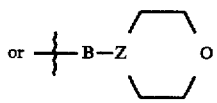

wherein
Z is N and

B is a group of the formulae

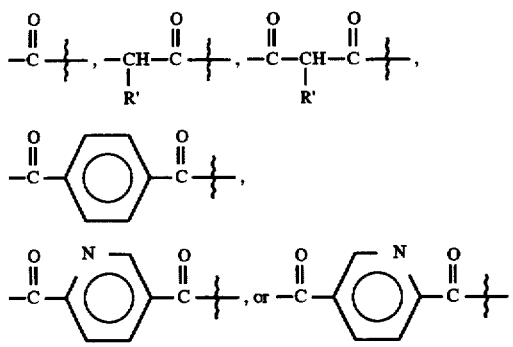

and wherein R' is hydrogen or a $C_{1-6}$alkyl group.
Specific examples of preferred compounds include:

(E)-N-[4-(4-Morpholinylcarbonyl)benzoyl]-L-valyl-N-[2-(acetyloxy)-3,3,4,4,4-pentafluoro-1-(1-methylethyl)-1-butenyl]-L-prolinamide;

(E)-N-[4-(4-Morpholinylcarbonyl)benzoyl]-L-valyl-N-[3,3,4,4,4-pentafluoro-1-(1-methylethyl)-2-(1-oxopropoxy)-1-butenyl]-L-prolinamide;

(E)-N-[4-(4-Morpholinylcarbonyl)benzoyl]-L-valyl-N-[3,3,4,4,4-pentafluoro-1-(1-methylethyl)-2-(2-methyl-1-oxopropoxy)-1-butenyl]-L-prolinamide;

(Z)-N-[4-(4-Morpholinylcarbonyl)benzoyl]-L-valyl-N-[2-(acetyloxy)-3,3,4,4,4-pentafluoro-1-(1-methylethyl)-1-butenyl]-L-prolinamide;

(E)-N-[(1,1-Dimethylethoxy)carbonyl]-L-alanyl-L-alanyl-N-[2-(acetyloxy)-3,3,3-trifluoro-1-(1-methylethyl)-1-propenyl]-L-prolinamide; (SEQ. ID NO. 2)

(E)-N-[4-(4-Morpholinylcarbonyl)benzoyl]-L-valyl-N-[2-(acetyloxy)-3,3,3-trifluoro-1-(1-methylethyl)-1-propenyl]-L-prolinamide;

(E)-N-(4-Morpholinylcarbonyl)-L-valyl-N-[2-(acetyloxy)-3,3,3-trifluoro-1-(1-methylethyl)-1-propenyl]-L-prolinamide;

(E)-N-[4-[(4-Chlorophenyl)sulfonylaminocarbonyl]benzoyl]-L-valyl-N-[2-(acetyloxy)-3,3,3-trifluoro-1-(1-methylethyl)-1-propenyl]-L-prolinamide.

(E)-N-(4-Morpholinylcarbonyl)-L-valyl-N-[2-(acetyloxy)-3,3,4,4,4-pentafluoro-1-(1-methylethyl)-1-butenyl]-L-prolinamide;

(Z)-N-(4-Morpholinylcarbonyl)-L-valyl-N-[2-(acetyloxy)-3,3,4,4,4-pentafluoro-1-(1-methylethyl)-1-butenyl]-L-prolinamide;

(E)-N-[4-(4-Morpholinylsulfonyl)benzoyl]-L-valyl-N-[2-(acetyloxy)-3,3,4,4,4-pentafluoro-1-(1-methylethyl)-1-butenyl]-L-prolinamide;

(Z)-N-[4-(4-Morpholinylsulfonyl)benzoyl]-L-valyl-N-[2-(acetyloxy)-3,3,4,4,4-pentafluoro-1-(1-methylethyl)-1-butenyl]-L-prolinamide;

(E)-N-[3-(3-Pyridyl)propanoyl]-L-valyl-N-[2-(acetyloxy)-3,3,4,4,4-pentafluoro-1-(1-methylethyl)-1-butenyl]-L-prolinamide;

(Z)-N-[3-(3-Pyridyl)propanoyl]-L-valyl-N-[2-(acetyloxy)-3,3,4,4,4-pentafluoro-1-(1-methylethyl)-1-butenyl]-L-prolinamide;

(E)-N-[4-(4-Morpholinylcarbonyl)benzoyl]-L-norvalyl-N-[2-(acetyloxy)-3,3,4,4,4-pentafluoro-1-(1-methylethyl)-1-butenyl]-L-prolinamide;

(Z)-N-[4-(4-Morpholinylcarbonyl)benzoyl]-L-norvalyl-N-[2-(acetyloxy)-3,3,4,4,4-pentafluoro-1-(1-methylethyl)-1-butenyl]-L-prolinamide;

(E)-N-[4-(4-Morpholinylcarbonyl)benzoyl]-L-alanyl-N-[2-(acetyloxy)-3,3,4,4,4-pentafluoro-1-(1-methylethyl)-1-butenyl]-L-prolinamide;

(Z)-N-[4-(4-Morpholinylcarbonyl)benzoyl]-L-alanyl-N-[2-(acetyloxy)-3,3,4,4,4-pentafluoro-1-(1-methylethyl)-1-butenyl]-L-prolinamide;

(E)-N-[4-(4-Morpholinylcarbonyl)benzoyl]-L-valyl-N-[2-(acetyloxy)-3,3,4,4,4-pentafluoro-1-(1-methylethyl)-1-butenyl]-L-2-azetamide;

(Z)-N-[4-(4-Morpholinylcarbonyl)benzoyl]-L-valyl-N-[2-(acetyloxy)-3,3,4,4,4-pentafluoro-1-(1-methylethyl)-1-butenyl]-L-2-azetamide;

(E)-N-[4-(4-Morpholinylcarbonyl)benzoyl]-L-valyl-N-[2-(acetyloxy)-3,3,4,4,4-pentafluoro-1-(1-methylethyl)-1-butenyl]-D,L-2-pipecolinamide;

(Z)-N-[4-(4-Morpholinylcarbonyl)benzoyl]-L-valyl-N-[2-(acetyloxy)-3,3,4,4,4-pentafluoro-1-(1-methylethyl)-1-butenyl]-D,L-2-pipecolinamide;

(E)-N-[4-(4-Morpholinylcarbonyl)benzoyl]-L-valyl-N-[2-(acetyloxy)-3,3,4,4,4-pentafluoro-1-(1-methylethyl)-1-butenyl]-trans-4-hydroxyprolinamide;

(Z)-N-[4-(4-Morpholinylcarbonyl)benzoyl]-L-valyl-N-[2-(acetyloxy)-3,3,4,4,4-pentafluoro-1-(1-methylethyl)-1-butenyl]-trans-4-hydroxyprolinamide;

(E)-N-[4-(4-Morpholinylcarbonyl)benzoyl]-L-valyl-N-[2-(acetyloxy)-3,3,4,4,4-pentafluoro-1-(1-methylethyl)-1-butenyl]-trans-4-acetoxyprolinamide;

(Z)-N-[4-(4-Morpholinylcarbonyl)benzoyl]-L-valyl-N-[2-(acetyloxy)-3,3,4,4,4-pentafluoro-1-(1-methylethyl)-1-butenyl]-trans-4-acetoxyprolinamide;

(E)-N-[4-(4-Morpholinylcarbonyl)benzoyl]-L-valyl-N-[2-(acetyloxy)-3,3,4,4,4-pentafluoro-1-(1-methylethyl)-1-butenyl]-trans-4-benzyloxyprolinamide;

(Z)-N-[4-(4-Morpholinylcarbonyl)benzoyl]-L-valyl-N-[2-(acetyloxy)-3,3,4,4,4-pentafluoro-1-(1-methylethyl)-1-butenyl]-trans-4-benzyloxyprolinamide;

(E)-N-[4-(4-Morpholinylcarbonyl)benzoyl]-L-valyl-N-[2-(acetyloxy)-3,3,4,4,4-pentafluoro-1-(1-methylethyl)-1-butenyl]-D,L-1,2,3,4-tetrahydro-3-isoquinolinamide;

(Z)-N-[4-(4-Morpholinylcarbonyl)benzoyl]-L-valyl-N-[2-(acetyloxy)-3,3,4,4,4-pentafluoro-1-(1-methylethyl)-1-butenyl]-D,L-1,2,3,4-tetrahydro-3-isoquinolinamide;

(E)-N-[4-(4-Morpholinylcarbonyl)benzoyl]-L-valyl-N-[2-(acetyloxy)-3,3,4,4,4-pentafluoro-1-(1-methylethyl)-1-butenyl]-L-1,2,3,4-tetrahydro-3-isoquinolinamide;

(Z)-N-[4-(4-Morpholinylcarbonyl)benzoyl]-L-valyl-N-[2-(acetyloxy)-3,3,4,4,4-pentafluoro-1-(1-methylethyl)-1-butenyl]-L-1,2,3,4-tetrahydro-3-isoquinolinamide;

(E)-N-[4-(4-Morpholinylcarbonyl)benzoyl]-L-valyl-N-[2-(acetyloxy)-3,3,4,4,4-pentafluoro-1-(1-methylethyl)-1-butenyl]-L-4-thiazolidinamide;

(Z)-N-[4-(4-Morpholinylcarbonyl)benzoyl]-L-valyl-N-[2-(acetyloxy)-3,3,4,4,4-pentafluoro-1-(1-methylethyl)-1-butenyl]-L-4-thiazolidinamide;

(E)-N-[4-(4-Morpholinylcarbonyl)benzoyl]-L-valyl-N-[2-(acetyloxy)-3,3,4,4,4-pentafluoro-1-(1-propyl)-1-butenyl]-L-prolinamide;

(Z)-N-[4-(4-Morpholinylcarbonyl)benzoyl]-L-valyl-N-[2-(acetyloxy)-3,3,4,4,4-pentafluoro-1-(1-propyl)-1-butenyl]-L-prolinamide;

(E)-N-[4-(4-Morpholinylcarbonyl)benzoyl]-L-valyl-N-[2-(acetyloxy)-3-fluoro-1-(1-methylethyl)-1-butenyl]-L-prolinamide;

(Z)-N-[4-(4-Morpholinylcarbonyl)benzoyl]-L-valyl-N-[2-(acetyloxy)-3-fluoro-1-(1-methylethyl)-1-butenyl]-L-prolinamide;

(E)-N-[4-(4-Morpholinylcarbonyl)benzoyl]-L-valyl-N-[2-(acetyloxy)-3,3-difluoro-1-(1-methylethyl)-1-butenyl]-L-prolinamide;

(Z)-N-[4-(4-Morpholinylcarbonyl)benzoyl]-L-valyl-N-[2-(acetyloxy)-3,3-difluoro-1-(1-methylethyl)-1-butenyl]-L-prolinamide;

In general, the compounds of Formula 1 may be prepared using standard chemical reactions analogously known in the art and as depicted in Scheme A, wherein the terms K, $P_4$, $P_3$, $P_2$, $R_1$, $R_2$, $R_3$ and $R_4$ are as defined in formula 1.

Scheme A

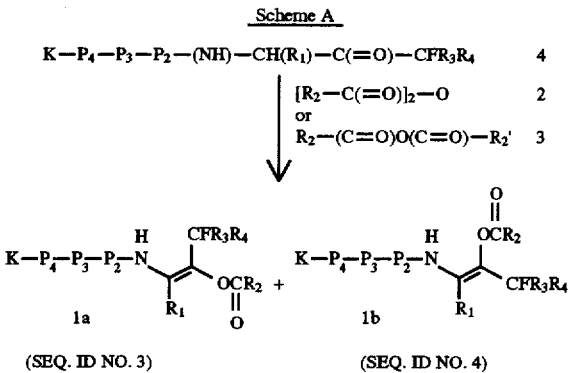

Generally, the acylated enols of formulae 1a and 1b may be formed by reacting the peptide of formula 4 with a suitable symmetrical anhydride 2 or a suitable mixed anhydride 3 (wherein $R_2'$ and $R_2$ are different but are both $R_2$ groups as defined above) in the presence of an amine base, such as the tertiary amines triethylamine and N-methylmorpholine or aromatic amines such as 4-dimethylaminopyridine as well as picolines, collidines and pyridine. The reactants may be contacted in a suitable organic solvent such as acetonitrile, methylene chloride, and the like. The reaction is typically carried out over a period of time ranging from about 30 minutes to about 48 hours at a temperature within the range of from about −40° C. to about 85° C. Generally, temperatures below 0° C. provide high ratios of 1a to 1b and 1a may be isolated in its pure form by chromatography or recrystallization. Generally, reaction temperatures greater than 0° C. provide increasing ratios of 1b to 1a and 1b may be isolated by chromatography or recrystallization.

Alternatively, the acylated enols of formulae 1a and 1b may be formed by reacting the peptide of formula 4 with a suitable acid halide of the formula $R_2$—C(=O)X (X=F, Cl, Br, I) in the presence of a weakly basic amine such as the picolines, collidines or pyridine.

European Patent Appl. Publ. No. 0529568 A1 discloses the compounds of formula 4 wherein K is

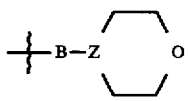

Z is N or CH; B is a group of the formulae

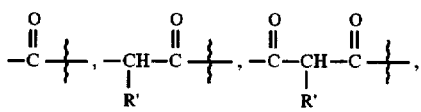

-continued

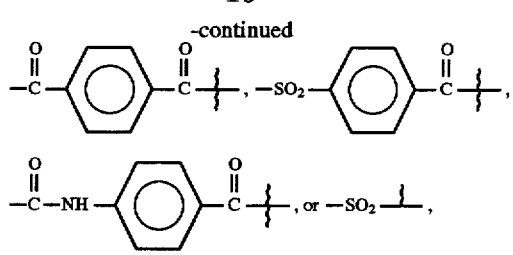

wherein R' is hydrogen or a $C_{1-6}$alkyl group; $R_3$ is —F; $R_4$ is —$CF_3$;

$R_1$ is the R-group of the amino acids Ala, bAla, Leu, Ile, Val, Nva, bVal, Met, Nle, Gly, or an N-methyl derivative;

$P_2$ is Ala, bAla, Leu, Ile, Val, Nva, bVal, Met, Nle, Gly, Phe, Tyr, Trp, or Nal(1) where the nitrogen of the alpha-amino group can be substituted with an R group where R is a $(C_{1-6})$alkyl, $(C_{3-12})$cycloalkyl, $(C_{3-12})$cycloalkyl$(C_{1-6})$alkyl, $(C_{4-11})$bicycloalkyl, $(C_{4-11})$bicycloalkyl$(C_{1-6})$alkyl, $(C_{6-10})$aryl, $(C_{6-10})$aryl$(C_{1-6})$alkyl, $(C_{3-7})$heterocycloalkyl, $(C_{3-7})$heterocycloalkyl$(C_{1-6})$alkyl, $(C_{5-9})$heteroaryl, $(C_{5-9})$heteroaryl$(C_{1-6})$alkyl, fused $(C_{6-10})$aryl$(C_{3-12})$cycloalkyl, fused $(C_{6-10})$aryl$(C_{3-12})$cyclo-alkyl$(C_{1-6})$alkyl, fused $(C_{5-9})$heteroaryl$(C_{3-12})$cyclo-alkyl, or fused $(C_{5-9})$heteroaryl$(C_{3-12})$cycloalkyl-$(C_{1-6})$alkyl, or $P_2$ is Pro, 1,2,3,4-tetrahydro-3-isoquinoline carboxylic acid (Tic), thiazolidine-4-carboxylic acid (Tca), or Ind;

$P_3$ is Ala, bAla, Leu, Ile, Val, Nva, bVal, Met, or Nle or an N-methyl derivative, Pro, Ind, Tic or Tca, or Lys substituted on its epsilon amino group (defined in the reference as the "omega" group) with a morpholino-B-group or Orn substituted on its delta amino group (defined in the reference as the "omega" group) with a morpholino-B-group; and $P_4$ is Ala, bAla, Leu, Ile, Val, Nva, bVal, Met, or Nle or an N-methyl derivative or a bond.

European Patent Appl. Publ. No. 0529568 A1 is enclosed herein by reference as if fully set forth.

Those compounds of formula 4 defined herein, but not disclosed in European Patent Appl. Publ. No. 0529568 A1, may be prepared by the following synthetic procedures which are well known and appreciated by one of ordinary skill in the art.

In general, all of the compounds of formula 4 may be prepared using standard chemical reactions analogously known in the art and as depicted in Scheme B.

Scheme B

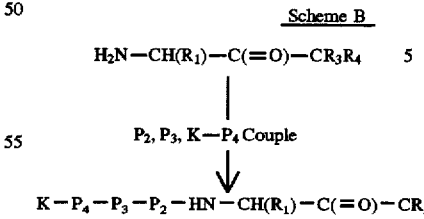

Scheme B provides a general synthetic scheme for preparing the compounds of formula 4.

The $P_2$, $P_3$ and K-$P_4$ groups can be linked to the free amino group of the amino acid derivative of structure 5. Note that structure 5 represents the $P_1$ moiety wherein the free carboxylic acid group has been substituted with a "$CR_3R_4$" moiety as defined above. The $P_2$, $P_3$ and K-$P_4$ can be linked to the unprotected, free amino compound ($P_1$-$CR_3R_4$) by well known peptide coupling techniques.

Furthermore, the $P_1$, $P_2$, $P_3$ and $K-P_4$ groups may be linked together in any order as long as the final compound is $K-P_4-P_3-P_2-P_1-CR_3R_4$. For example, $K-P_4$ can be linked to $P_3$ to give $K-P_4-P_3$ which is linked to $P_2-P_1-CR_3R_4$; or $K-P_4$ linked to $P_3-P_2$ then linked to an appropriately C-terminal protected $P_1$ and the C-terminal protecting group converted to $CR_3R_4$.

Generally, peptides are elongated by deprotecting the α-amine of the N-terminal residue and coupling the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme B, or by condensation of fragments (two to several amino acids), or combination of both processes, or by solid phase peptide synthesis according to the method originally described by Merrifield, *J. Am. Chem. Soc.*, 1963, 85, 2149–2154, the disclosure of which is hereby incorporated by reference. When a solid phase synthetic approach is employed, the C-terminal carboxylic acid is attached to an insoluble carrier (usually polystyrene). These insoluble carriers contain a group which will react with the carboxylic acid group to form a bond which is stable to the elongation conditions but readily cleaved later. Examples of which are: chloro- or bromomethyl resin, hydroxymethyl resin, and aminomethyl resin. Many of these resins are commercially available with the desired C-terminal amino acid already incorporated.

Alternatively, compounds of the invention can be synthesized using automated peptide synthesizing equipment. In addition to the foregoing, peptide synthesis are described in Stewart and Young, "Solid Phase Peptide Synthesis", 2nd ed., Pierce Chemical Co., Rockford, Ill. (1984); Gross, Meienhofer, Udenfriend, Eds., "The Peptides: Analysis, Synthesis, Biology", Vol 1, 2, 3, 5 and 9, Academic Press, New York, 1980–1987; Bodanszky, "Peptide Chemistry: A Practical Textbook", Springer-Verlag, New York (1988); and Bodanszky, et al. "The Practice of Peptide Synthesis" Springer-Verlag, New York (1984), the disclosures of which are hereby incorporated by reference.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxy-succinic imido ester) method, Woodward reagent K method, carbonyldiimidazole method, phosphorus reagents such as BOP-Cl, or oxidation-reduction methods. Some of these methods (especially the carbodiimide method) can be enhanced by adding 1-hydroxybenzotriazole. These coupling reactions can be performed in either solution (liquid phase) or solid phase.

The functional groups of the constituent amino acids generally must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1981), the disclosure of which is hereby incorporated by reference.

The n-carboxyl group of the C-terminal residue is usually, but does not have to be, protected by an ester that can be cleaved to give the carboxylic acid. Protecting groups which can be used include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters.

The α-amino group of each amino acid to be coupled to the growing peptide chain must be protected. Any protecting group known in the art can be used. Examples of which include: 1) acyl types such as formyl, trifluoroacetyl, phthalyl, and p-toluenesulfonyl; 2) aromatic carbamate types such as benzyloxycarbonyl (Cbz or Z) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. The preferred α-amino protecting group is either Boc or Fmoc, preferably Boc. Many amino acid derivatives suitably protected for peptide synthesis are commercially available.

The α-amino protecting group of the newly added amino acid residue is cleaved prior to the coupling of the next amino acid. When the Boc group is used, the methods of choice are trifluoroacetic acid, neat or in dichloromethane, or HCl in dioxane or ethyl acetate. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidine in dimethylformamide, but any secondary amine or aqueous basic solutions can be used. The deprotection is carried out at a temperature between 0° C. and room temperature.

Any of the amino acid bearing side chain functionalities must be protected during the preparation of the peptide using any of the above-described groups. Those skilled in the art will appreciate that the selection and use of appropriate protecting groups for these side chain functionalities depends upon the amino acid and presence of other protecting groups in the peptide. The selection of such protecting groups is important in that it must not be removed during the deprotection and coupling of the α-amino group.

For example, when Boc is used as the α-amino protecting group, the following side chain protecting groups are suitable: p-toluenesulfonyl (tosyl) moieties can be used to protect the amino side chains of amino acids such as Lys and Arg; p-methylbenzyl, acetamidomethyl, benzyl (Bzl), or t-butylsulfonyl moieties can be used to protect the sulfide containing side chains of amino acids such as cysteine; and benzyl (Bzl) ether can be used to protect the hydroxy containing side chains of amino acids such as Ser or Thr.

When Fmoc is chosen for the α-amine protection usually tert-butyl based protecting groups are acceptable. For instance, Boc can be used for lysine, tert-butyl ether for serine and threonine and tert-butyl ester for glutamic acid.

Once the elongation of the peptide is completed all of the protecting groups are removed. When a solution phase synthesis is used, the protecting groups are removed in whatever manner is dictated by the choice of protecting groups. These procedures are well known to those skilled in the art.

When a solid phase synthesis is used, the peptide is cleaved from the resin usually simultaneously with the protecting group removal. When the Boc protection scheme is used in the synthesis, treatment with anhydrous HF containing additives such as dimethyl sulfide, anisole, thioanisole, or p-cresol at 0° C. is the preferred method for cleaving the peptide from the resin. The cleavage of the peptide can also be accomplished by other acidic reagents such as trifluoromethanesulfonic acid/trifluoroacetic acid mixtures. If the Fmoc protection scheme is used the N-terminal Fmoc group is cleaved with reagents described earlier. The other protecting groups and the peptide are cleaved from the resin using a solution of trifluoroacetic acid and various additives such as anisole, etc.

Alternatively, the compounds of formula 4 may be prepared using standard chemical reactions analogously known in the art and as depicted in Scheme C.

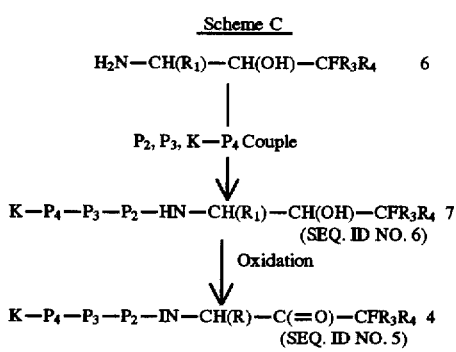

Scheme C provides an alternative general synthetic scheme for preparing the compounds of formula 4.

The $P_2$, $P_3$ and K-$P_4$ groups can be linked to the free amino group of the amino alcohol derivative of structure 6 as described previously in Scheme B to give the peptido alcohol of structure 7.

The alcohol functionality of the peptido alcohol of structure 7 is then oxidized by techniques and procedures well known and appreciated by one of ordinary skill in the art, such as a Swern Oxidation using oxalyl chloride and dimethylsulfoxide, to give the compounds of formula 4.

Starting materials for use in Schemes B and C are readily available to one of ordinary skill in the art. For example, amino acids $P_2$, $P_3$ and K-$P_4$ wherein K is hydrogen are commercially available. In addition, amino protecting group K wherein K is acetyl, succinyl, benzoyl, t-butyloxycarbonyl, carbobenzyloxy, tosyl, dansyl, isovaleryl, methoxysuccinyl, 1-adamantanesulphonyl, 1-adamantaneacetyl, 2-carboxbenzoyl, phenylacetyl, t-butylacetyl, bis [(1-naphthyl)methyl]acetyl or -A-$R_z$ wherein A is

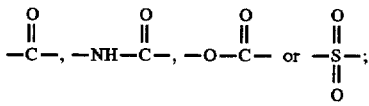

and Rz is an aryl group containing 6, 10 or 12 carbons suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino wherein the alkyl group contains 1 to 6 carbons, 5-tetrazolyl, and acylsulfonamido (i.e., acylaminosulfonyl and sulfonylaminocarbonyl) containing from 1 to 15 carbons, provided that when the acylsulfonamido contains an aryl the aryl may be further substituted by a member selected from fluoro, chloro, bromo, iodo and nitro; and such other terminal amino protecting groups which are functionally equivalent thereto are described in European Patent Application OPI No. 0363284, Apr. 11, 1990. Furthermore, dimethyl carbamoyl chloride is commercially available and

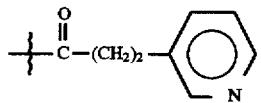

is available via a literature preparation [J. Amer. Chem. Soc. (1980), 102, 5530–8] for compounds of formula 1 wherein K is —C(O)N—(CH$_3$)$_2$, or

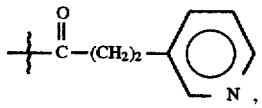

respectively. Synthetic procedures for converting said compounds into K-$P_4$ substituents are well known and appreciated by one of ordinary skill in the art.

Starting amino compounds of formula 5 are readily available to one of ordinary skill in the art. For example, certain protected amino compounds of formula 5 wherein CFR$_3$R$_4$ is —CF$_3$, —CHF$_2$, —CF$_2$C(=O)NHR$_6$' or —CF$_2$C(=O)OR$_6$' (wherein R$_6$'=C$_{1-4}$ straight or branched alkyl, phenyl, cyclohexyl, cyclohexylmethyl or benzyl) are described in European Patent Application OPI No. 0195212, inventors Michel Jung et al., with a publication date of Sep. 24, 1986. In addition, amino compounds of formula 5 wherein CFR$_3$R$_4$ is —CF$_3$, —CF$_2$(CH$_2$)$_t$CH$_3$ (wherein t=2, 3 or 4), or —CF$_2$CF$_3$ are described in European Patent Application OPI No. 0503203, Sep. 16, 1992. Amino compounds of formula 5 wherein CFR$_3$R$_4$ is —CFH$_2$ are described in Biochem. J. (1987), 241, 871–5, Biochem. J. (1986), 239, 633–40 and U.S. Pat. No. 4,518,528, May 21, 1985. Amino compounds of formula 5 wherein CFR$_3$R$_4$ is —CF$_2$CF$_3$ are described in European Patent Application Publ. No. 0410411, inventors Bey et al., with a publication date of Jan. 30, 1991, as well as in European Patent Application OPI No. 0529568, inventors Peet et al., with a publication date of Mar. 3, 1993. Likewise, amino compounds of formula 5 wherein CFR$_3$R$_4$ is CF$_2$C(=O)NHR$_6$' (wherein R$_6$' is (C$_{1-6}$) alkyl, aryl or arylalkyl) are described in Patent Application No. PCT/US91/09741, inventors Daniel Schirlin et al., filed Dec. 20, 1991. The above references are incorporated herein by reference as if fully set forth.

In addition, other starting materials for use in Schemes B and C may be prepared by the following synthetic procedures which are well known and appreciated by one of ordinary skill in the art.

Substituted amino acids K-$P_4$ of structure wherein K is

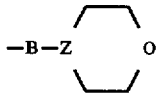

wherein
Z is N or CH, and
B is a group of the formulae

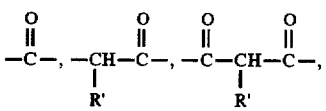

-continued

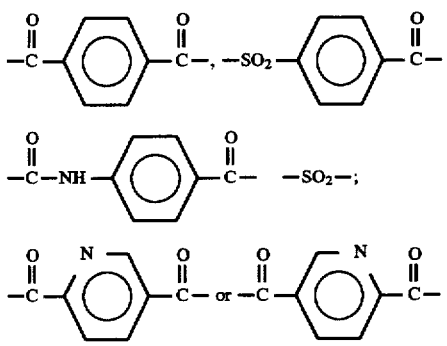

wherein R' is hydrogen or a $C_{1-6}$ alkyl group are prepared using standard chemical reactions analogously known in the art.

The procedure for preparing the substituted amino acids K-P$_4$ wherein K is

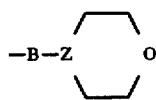

wherein B is a —C(=O)— is outlined in Scheme D wherein P$_4$ and Z are as previously defined or are the functional equivalents of these groups.

Scheme D

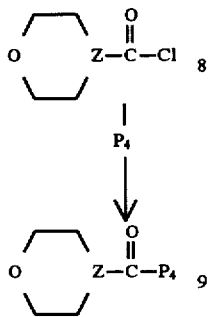

Specifically the amino acids K-P$_4$ wherein K is

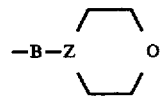

wherein B is a —C(=O)— are prepared by coupling of the amino acid K-P$_4$ wherein K is hydrogen with an acid chloride of structure 8 in the presence of from one to four molar equivalents of a suitable amine which can act as a hydrogen halide acceptor. Suitable amines for use as hydrogen halide acceptors are tertiary organic amines such as tri-(lower alkyl)amines, for example, triethylamine, or aromatic amines such as picolines, collidines, and pyridine. When pyridines, picolines, or collidines are employed, they can be used in high excess and act therefore also as the reaction solvent. Particularly suitable for the reaction is N-methylmorpholine ("NMM"). The coupling reaction can be performed by adding an excess, such as from 1–5, preferably about a 4-fold molar excess of the amine and then the acid chloride of structure 8, to a solution of the amino acid K-P$_4$ wherein K is hydrogen. The solvent can be any suitable solvent, for example, petroleum ethers, a chlorinated hydrocarbon such as carbon tetrachloride, ethylene chloride, methylene chloride, or chloroform; a chlorinated aromatic such as 1,2,4-trichlorobenzene, or o-dichlorobenzene; carbon disulfide; an ethereal solvent such as diethylether, tetrahydrofuran, or 1,4-dioxane, or an aromatic solvent such as benzene, toluene, or xylene. Methylene chloride is the preferred solvent for this coupling reaction. The reaction is allowed to proceed for from about 15 minutes to about 6 hours, depending on the reactants, the solvent, the concentrations, and other factors, such as the temperature which can be from about 0° C. to about 60° C., conveniently at about room temperature, i.e. 25° C. The N-protected amino acids K-P$_4$ wherein K is

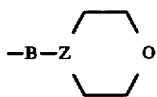

wherein B is a —C(=O)— can be isolated from the reaction mixture by any appropriate techniques such as by chromatography on silica gel.

The substituted amino acids K-P$_4$ wherein K is

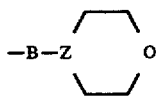

wherein B is other than a —C(=O)— can be prepared analogously, merely by substituting the appropriate intermediate

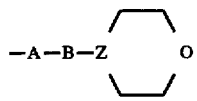

wherein B is other than a —C(=O)— and A is Cl or OH (the corresponding acid, acid chloride or sulphonyl chloride) for the compound of structure 8 in Scheme D.

The acid chloride of structure 8 and the appropriate intermediate of formula

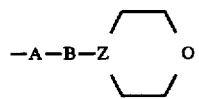

wherein B is other than a —C(=O)— and A is Cl or OH (the corresponding acid, acid chloride or sulphonyl chloride) are commercially available or may be readily prepared by techniques and procedures well known and appreciated by one of ordinary skill in the art.

For example, the appropriate intermediates of formula

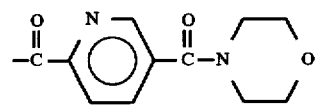

may be prepared as outlined in Scheme E wherein all substituents are as previously defined.

Scheme E

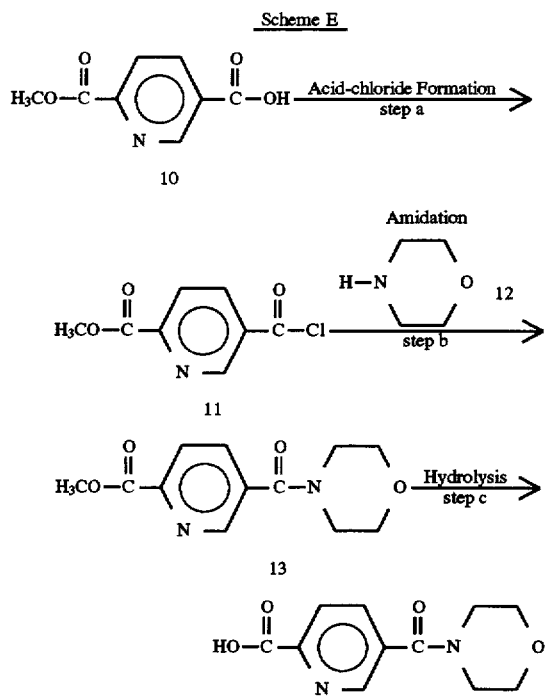

Scheme E provides a general synthetic procedure for preparing the appropriate intermediates of formula

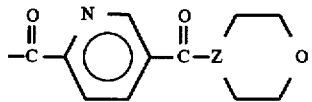

wherein Z is as previously defined.

In step a, the carboxylic acid functionality of the appropriate 2,5-pyridinedicarboxylic acid, 2-methyl ester 10 (*Nippon Kagaku Zasshi*, 1967, 88, 563) is converted to its acid chloride using techniques and procedures well known and appreciated by one of ordinary skill in the art, such as thionyl chloride, to give the corresponding 6-carbomethoxynicotinoyl chloride 11.

In step b, the acid chloride 11 is amidated with morpholine 12 by techniques and procedures well known and appreciated by one of ordinary skill in the art to give the corresponding 5-(morpholine-4-carbonyl)-2-pyridinecarboxylic acid, methyl ester 13.

In step c, the methyl ester functionality of 13 is hydrolyzed by techniques and procedures well known and appreciated by one of ordinary skill in the art, with for example, lithium hydroxide in methanol, to give 5-(morpholine-4-carbonyl)-2-pyridinecarboxylic acid 14.

In addition, the appropriate intermediate of formula

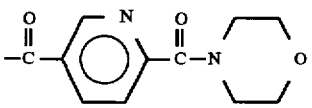

may be prepared as outlined in Scheme F wherein all substituents are as previously defined.

Scheme F

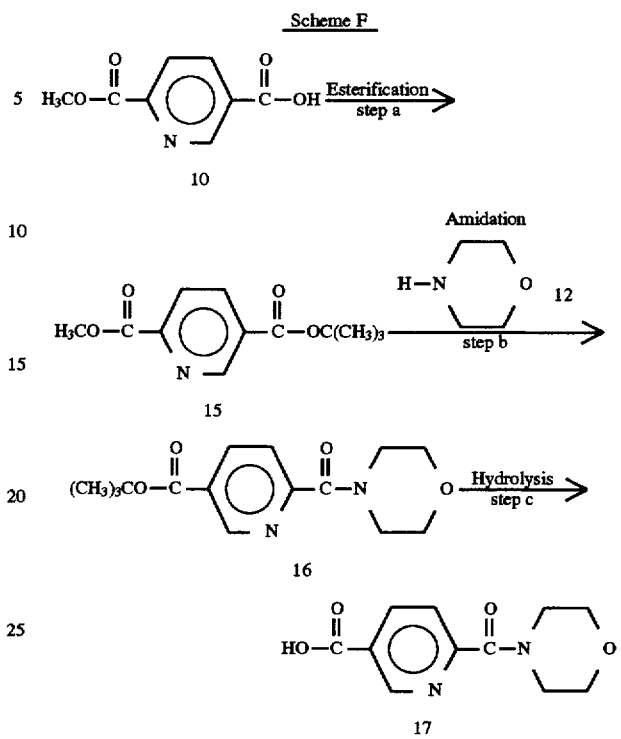

Scheme F provides a general synthetic procedure for preparing the appropriate intermediates of formula

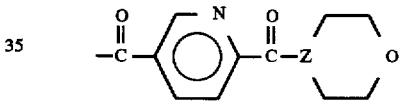

wherein Z is as previously defined.

In step a, the free carboxylic acid functionality of 2,5-pyridinedicarboxylic acid, 2-methyl ester 10 (*Nippon Kagaku Zasshi*, 1967, 88, 563) is converted to its t-butyl ester using techniques and procedures well known and appreciated by one of ordinary skill in the art, such as the t-butyl alcohol adduct of dicyclohexylcarbodiimide (*Synthesis*, 1979, 570), to give the corresponding 2,5-pyridinedicarboxylic acid, 2-methyl ester, 5-t-butyl ester 15.

For example, the 2,5-pyridinedicarboxylic acid, 2-methyl ester 10 is combined with a molar excess of the t-butyl alcohol adduct of dicyclohexylcarbodiimide in an appropriate organic solvent, such as methylene chloride. The reaction is typically conducted at a temperature range of from 0° C. to room temperature and for a period of time ranging from 2–24 hours. The 2,5-pyridinedicarboxylic acid, 2-methyl ester, 5-t-butyl ester 15 is isolated from the reaction mixture by standard extractive methods as is known in the art and may be purified by crystallization.

In Step b, the methyl ester functionality of 15 is amidated with morpholine 12 to give the corresponding 6-(morpholine-4-carbonyl)nicotinic acid, t-butyl ester 16.

For example, the 2,5-pyridinedicarboxylic acid, 2-methyl ester, 5-t-butyl ester 15 is contacted with a molar excess of morpholine in an appropriate organic solvent, such as tetrahydrofuran. The reaction is typically conducted at a temperature range of from room temperature to reflux and for a period of time ranging from 5 hours to 3 days. The 6-(morpholine-4-carbonyl)nicotinic acid, t-butyl ester 16 is isolated from the reaction mixture by standard extractive methods as is known in the art and may be purified by crystallization.

In step c, the t-butyl ester functionality of 16 is hydrolyzed, with for example, HCl in nitromethane, to give the corresponding 6-(morpholine-4-carbonyl)nicotinic acid 17.

In general, the compounds of formula 4 may be prepared using standard chemical reactions analogously known in the art. For those compounds of formula 4 where $CFR_3R_4$ is —$CF_2H$, —$CFH_2$ or —$CF_3$, intermediates for the application of the standard peptide coupling techniques are compounds of formula IIa–b wherein X' is $CFR_3R_4$ when $CFR_3R_4$ is —$CF_3$,

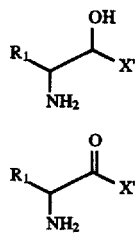

—$CFH_2$ or —$CF_2H$, and $R_1$ is as previously defined in formula 1. Similarly, designations $P_2$, $P_3$, $P_4$, and K shown in the foregoing schemes are as defined in formula 1, except that any subgeneric or other modifications thereof are highlighted by the use of a primed symbol with a specific designation for such modified symbol. Note that in scheme G, the designation "X'" is used to denote a subgeneric modification of the $CFR_3R_4$ group. The preparation and application of these compounds are depicted in scheme G.

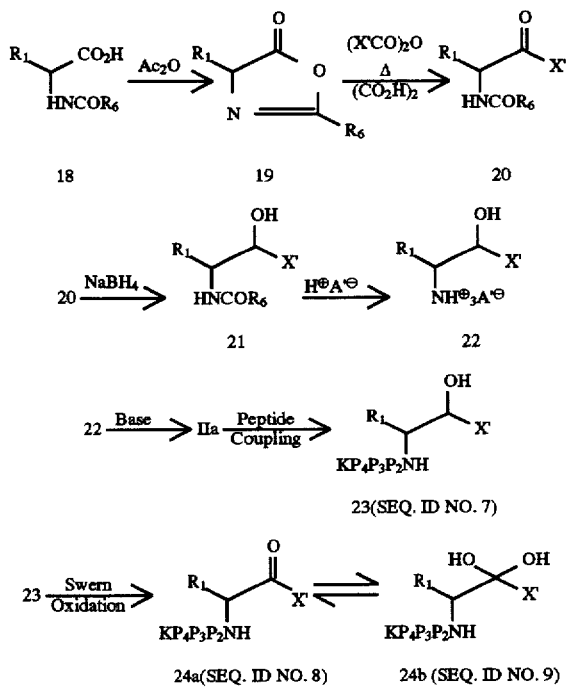

wherein $R_6$ is phenyl or other equivalent moiety, and X' is —$CF_2H$ or —$CF_3$. $H^\oplus$ $A'^\ominus$ means an acid. All the substituents, unless otherwise indicated, are as previously defined. The reagents and starting materials are readily available to one of ordinary skill in the art.

In general the formation of the substituted azlactones 19 is effected from the N-protected amino acids 18 by standard reaction conditions wherein the amino acid derivative 18 is heated in the presence of an acid anhydride. The so-produced azlactone 19 is reacted with a di- or trifluoroacetic acid anhydride or acid halide to give a fluorinated intermediate which (with or without isolation) is treated with anhydrous oxalic acid to produce the N-protected fluorinated ketone 20 whereupon the ketone is chemically reduced to its alcoholic amide 21. The amide 21 is cleaved under standard acidic conditions to yield its amide acid salt [e.g., its hydrochloride 22]. After neutralization, the alcohols IIa may be coupled to $KP_4P_3P_2OH$ using standard peptide chemistry techniques to produce compounds 23 which are subjected to the Swern oxidation procedure to obtain the desired product 24a and 24b (the ketone or hydrate respectively). Alternatively, the alcohols IIa may be oxidized to the ketones IIb which are coupled to $KP_4P_3P_2OH$ according to standard peptide chemistry techniques. When employing this alternative route, the amino moiety is first protected with a Boc protecting group, the OH function oxidized to its ketone via Swern oxidation procedures, and then the Boc protecting group removed and the resulting compounds IIb are the coupled to $KP_4P_3P_2OH$.

Scheme G is also applicable for the preparation of compounds of formula 4 wherein $CFR_3R_4$ is —$CF_2R_4'$ wherein $R_4'$ is $(C_{1-8})$alkyl, $(C_{3-12})$cycloalkyl, $(C_{6-10})$aryl or $(C_{6-10})$aryl$(C_{1-6})$alkyl, the substituted azlactones 19 being treated with an acid halide in the presence of a base such as triethylamine, followed by 4-dimethylaminopyridine (Tetrahedron Letters, 1986, 4437–4440).

Likewise, scheme G is also applicable for the preparation of compounds of formula 4 wherein $CFR_3R_4$ is —$CF_2CF_3$, the substituted azlactones 19 being treated with pentafluoropropanoic acid anhydride or acid halide.

An alternate route for the preparation of compounds of formula 4 wherein $CFR_3R_4$=—$CF_2CF_3$, is shown in scheme H.

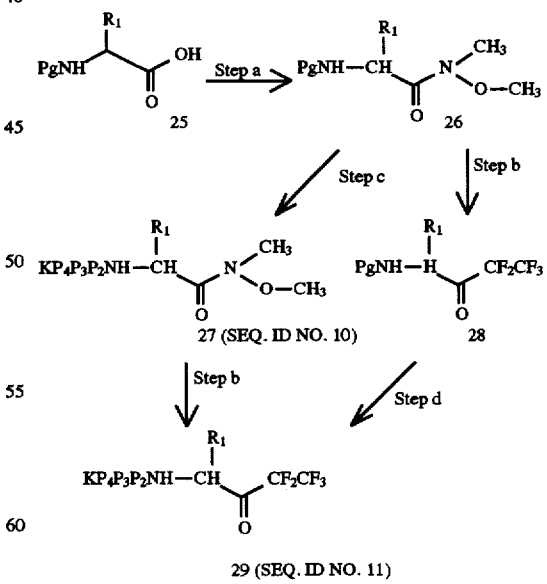

The required starting material defined by compound 25 is readily available either commercially or by applying known prior art principles and techniques. The term "Pg" refers to a suitable protecting group as more fully defined previously.

In Scheme H, step a the protected amino acid 25 is transformed into the hydroxamate 26. This amidation can be performed utilizing a coupling reaction as between two amino acids using the protected amino acid 25 and the N-alkyl O-alkylhydroxylamine. The standard coupling reaction can be carried out using standard coupling procedures as described previously for the coupling between two amino acids to provide the hydroxamate 26.

In step b, the protected hydroxamate 26 is transformed into the protected pentafluoroketone 28 [or 29]. This reaction can be performed utilizing a reaction of the type described in the following reference M. R. Angelastro, J. P Burkhart, P. Bey, N. P. Peet, Tetrahedron Letters, 33 (1992), 3265–3268.

In step c, the hydroxamate 26 is deprotected under conditions well known in the art as described by T. H. Green "Protection Groups in Organic Synthesis", John Wiley and Sons, 1981, Chapter 7, to provide the deprotected hydroxamate. The deprotected hydroxamate is elongated by coupling the next suitably protected amino acid through a peptide linkage using the methods previously described in Scheme G, or by condensation of fragments, or combination of both processes to provide the elongated peptide 27.

In step d, the ketone 28 is deprotected under conditions as previously described. The deprotected ketone 28 is elongated by coupling the next suitably protected amino acid through a peptide linkage using the methods previously described in Scheme G, or by condensation of fragments, or combination of both processes to provide the elongated ketone 29.

Alternatively, the corresponding protected amino acid ester of 25 [i.e. PgNH—CH($R_1$)C(=O)O$R_4$', 26a, wherein $R_4$' is as defined above] can be substituted for the hydroxamate 26. The corresponding protected amino acid esters of 25 are commercially available or easily synthesized from 25 by procedures well known by one of ordinary skill in the art. In step b, the amino acid ester 26a, is transformed into the protected pentafluoroketone 28 [or 29.] in a manner directly analogous to that used for the corresponding hydroxamate. Steps c and d would be the same as those employed when utilizing the hydroxamate 26.

Sheme H is also applicable for the preparation of compounds of formula 4 wherein $CFR_3R_4$ is —$CF_2CF_2CF_3$ or —$CF_2CF_2CF_2CF_3$, the amino acid ester 26a being alkylated with from 4–8 equivalents of perfluoropropyl iodide or perfluorobutyl iodide in the presence of from 4–8 equivalents of MeLi/LiBr in a suitable anhydrous solvent, such as ether, THF or toluene; the reaction being carried out at reduced temperature of from −100° C. to 0° C., preferably from −30° C. to −80° C. to provide the protected perfluoropropyl amino ketone and the protected perfluorobutyl amino ketone, respectively. Steps c and d would be the same as those employed when utilizing the hydroxamate 26.

For the preparation of compounds of formula 4 wherein $CFR_3R_4$ is $CF_2C(=O)$—$NR_5R_6$, wherein $R_5$ and $R_6$ are as defined in Formula 1, scheme I may be used.

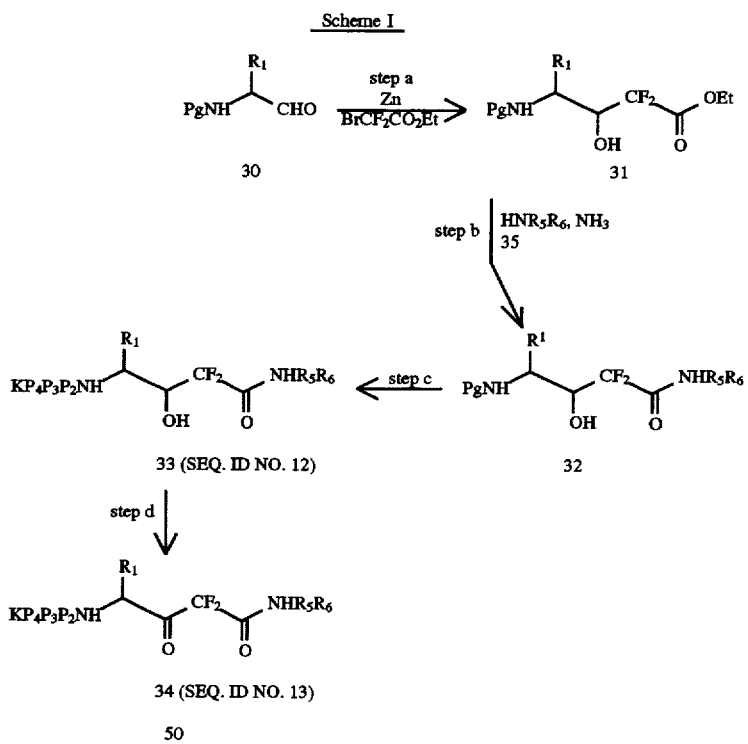

Scheme I

In effecting the steps of scheme I it is preferred to start with the aldehyde 30 wherein the protecting group is a carbamate preferably wherein Pg is benzyloxycarbonyl (CBZ). This so-protected aldehyde is subjected to a condensation reaction with an ester of bromodifluoroacetic acid, preferably the ethyl ester in the presence of zinc. Preferably the reaction is conducted in an anhydrous aprotic solvent, e.g., tetrahydrofuran, ether, dimethoxyethane and the like under a nitrogen atmosphere. The reaction mixture is gently heated under reflux conditions, preferably to about 60° C. for about 1–12 hours. Ester 31 in scheme I is converted to the secondary or tertiary amide 32 by treatment with the corresponding primary amines 35 under anhydrous conditions, preferably using such solvents as THF. The amidation is initiated at 0° C. or at room temperature and the reaction mixture might be heated to reflux for completion of the reaction.

In step c, the so-formed amide 32 is deprotected under conditions well known in the art as described by T. H. Green, "Protective Groups in Organic Synthesis", John Wiley and Sons, 1981, Chapter 7, to provide the deprotected amide of structure 32. The deprotected amide is elongated by coupling the next suitably protected amine and through a peptide linkage using the methods previously described in scheme B or by condensation of fragments, or by combination of both processes to provide the elongated peptide 33.

In step d the alcohol functionality of the alcohol 33 is then oxidized by techniques and procedures well known and appreciated of one ordinary skill in the art, such as Swern oxidation using oxalyl chloride and dimethylsulfoxide, to give the compounds of formula 34.

For the preparation of compounds of formula 4 wherein $CFR_3R_4$ is $CF_2C(=O)-OR_5$, wherein $R_5$ is as defined in Formula 1, scheme J may be used.

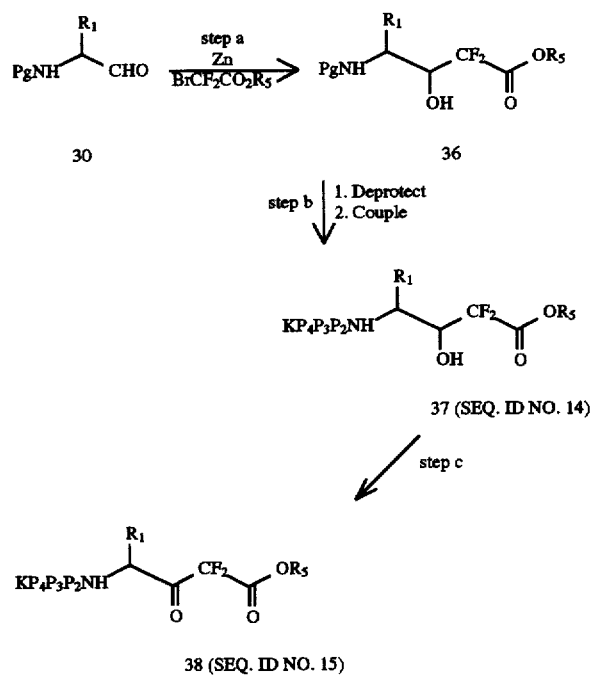

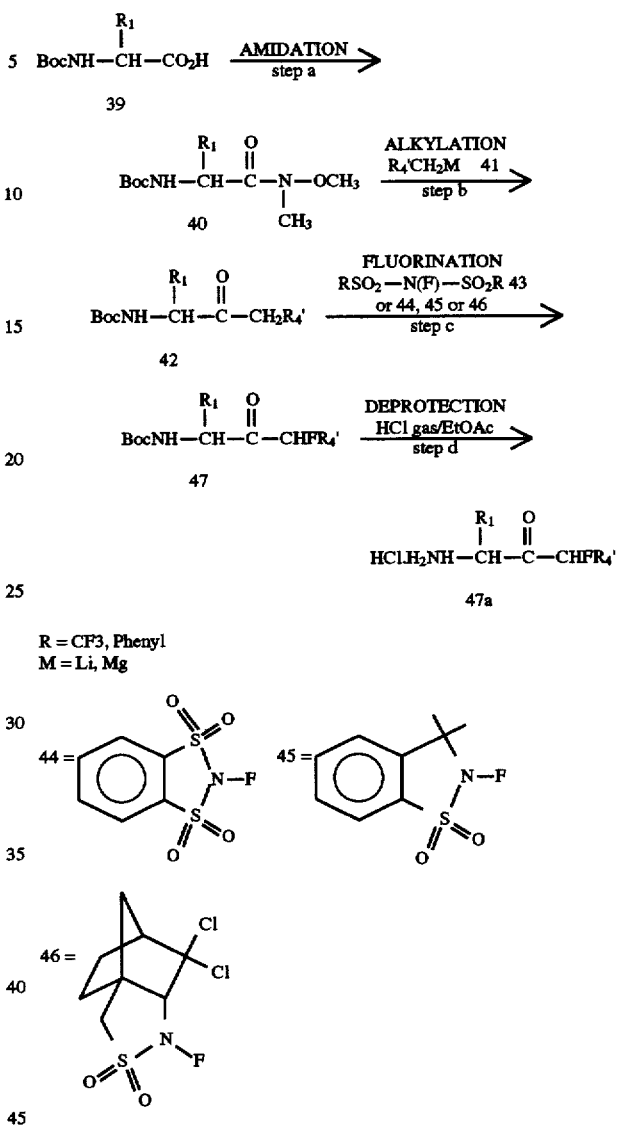

Step a is similar to Scheme I, step a and is applicable to all definitions of $R_5$. Likewise, scheme J, step b is the same or similar as that employed in scheme I, step c and scheme J, step c is the same or similar as that employed in scheme I, step d.

All of the amino acids employed in the synthesis of Formula 1 are either commercially available or are easily synthesized. For example, the amino acid derivative Pro(4-OAc) defined in $P_2$ can be made by esterifying a Pro residue by utilizing techniques well-known by one of ordinary skill in the art.

In addition, amino compounds of structure 5 wherein $CFR_3R_4$ is $-CHFR_4'$ wherein $R_4'$ is $(C_{1-8})$alkyl, $(C_{3-12})$ cycloalkyl, $(C_{6-10})$aryl or $(C_{6-10})$aryl$(C_{1-6})$alkyl, may be prepared as described in Scheme K wherein all substituents are as previously defined. Note that while the amino group is protected by t-butyloxycarbonyl, other suitable amino protecting groups, as described above, may be substituted by those skilled in the art.

In step a, the appropriate acid of structure 39 is amidated with N-methyl-N-methoxyamine by techniques and procedures well known and appreciated by one of ordinary skill in the art, such as a coupling reaction using 1,3-dicyclohexylcarbodiimide (DCC) and 1-hydroxybenzotriazole (HOBT) to give the corresponding amide of structure 40.

In step b, the appropriate amide of structure 40 is alkylated with the appropriate alkyl metal compound of structure 41 to give the corresponding keto compound of structure 42.

For example, the appropriate amide of structure 40 is treated with the alkyl metal compound of structure 41 in a suitable aprotic, anhydrous organic solvent such as tetrahydrofuran or diethyl ether. The reaction is typically conducted at a temperature range of from −78° C. to −40° C. and for a period of time ranging from 30 minutes to 5 hours. The corresponding keto compound of structure 42 is recovered from the reaction zone by extractive methods as is known in the art and may be purified by chromatography.

In step c, the appropriate keto compound of structure 42 is fluorinated with the N-fluorosulfonimide compound of structure 43, or the alternative fluorination reagents 44, 45 or 46 to give the protected amino compounds of structure 47 which is the amino compound of structure 5 in which the amino terminal group is substituted with a Boc group and $CPR_3R_4$ is —$CHFR_4'$.

For example, the appropriate keto compound of structure 42 is treated with an appropriate non-nucleophilic base, such as lithium diisopropylamide in a suitable anhydrous aprotic organic solvent, such as tetrahydrofuran at a temperature range of from −78° C. to −40° C. and for a period of time ranging from 5 minutes to 2 hours. The reaction mixture is then treated with the N-fluorosulfonimide compound of structure 42 and the reaction conducted at a temperature range of from −78° C. to −40° C. and for a period of time ranging from 30 minutes to 10 hours. The N-t-Boc protected amino compounds of structure 5 wherein $CFR_3R_4$ is —$CHFR_4'$ is recovered from the reaction zone by extractive methods as is known in the art and may be purified by chromatography.

The following examples present typical syntheses. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "mp" refers to melting point; "°C." refers to degrees Celsius; "mm Hg" refers to millimeters of mercury; "μL" refers to microliters; "μg" refers to micrograms; and "μM" refers to micromolar; "$Et_3N$" refers to triethylamine; "$CH_2Cl_2$" refers to methylene chloride; "EtOAc" refers to ethyl acetate; "NMM" refers to N-methylmorpholine; "IBCF" refers to isobutyl chloroformate; "DMF" refers to N,N-dimethylformamide. Combustion analyses fell within ±0.4% of the calculated values. NMR spectra were obtained in $CDCl_3$ unless otherwise noted. $^1H$ and $^{13}CNMR$ signals are reported in ppm from tetramethylsilane and $^{19}FNMR$ signals are reported in ppm from $CFCl_3$. Coupling constants are reported in Hertz (Hz).

EXAMPLE 1

Preparation of (E)-N-[4-(4-Morpholinylcarbonyl)benzoyl]-L-valyl-N-[2-(acetyloxy)-3,3,4,4,4-pentafluoro-1-(1-methylethyl)-1-butenyl]-L-prolinamide To a stirred solution of N-[4-(4-morpholinylcarbonyl)benzoyl]-L-valyl-N-[3,3,4,4,4-pentafluoro-1-(1-methylethyl)-2-oxobutyl]-L-prolinamide (2.00 g, 3.16 mmole, EP Pat. Appl. Publ. No. 0 529 568 A1), $Et_3N$ (0.66 mL, 4.74 mmole) and 4-dimethylaminopyridine (0.77 g, 6.32 mmole) in $CH_2Cl_2$ (8 mL) under $N_2$ atmosphere and cooled to −20° C. (dry ice-$CCl_4$ bath), add acetic anhydride (0.89 mL, 9.48 mmole), dropwise and over a five (5) minute period. After 1.5 hours at −20° C., dilute the reaction mixture with $CH_2Cl_2$ (70 mL) and wash the organics with 0.5N aqueous hydrochloric acid (2×50 mL) followed by 50 mL of a mixture of 0.5N aqueous hydrochloric acid-brine (1:9). Drying ($MgSO_4$) and concentration gives the crude product. The crude product can be recrystallized from ethyl acetate-hexane to provide the title compound as a white crystalline solid (MDL 103,279; 2.25 g, 85% yield, two crops), mp 127°–137° C. (dec).

TLC $R_f$ 0.34 (1:9 acetone-EtOAc).

$^1$HNMR δ 8.02 (br s, 1H, NHC=C), 7.88–7.84 (m, 2H, ½ aryl), 7.51–7.46 (m, 2H, ½ aryl), 6.85 (br d, 1H, J=8.9 Hz, NH), 4.87 (dd, 1H, J=6.3, 8.8 Hz, CH), 4.65 (dd, 1H, J=2.6, 8.0 Hz, CH), 3.92–3.54 (m, 8H), 3.39 (br s, 2H), 2.73 (septet, 1H, J=6.9 Hz, CHC=C), 2.52–2.42 (m, 1H), 2.24 (s, 3H, $COCH_3$), 2.25–1.85 (m, 4H), 1.08 (d, 3H, J=6.9 Hz, $CH_3$), 1.07 (d, 3H, J=6.7 Hz, $CH_3$), 1.05 (d, 3H, J=6.8 Hz, $CH_3$), 1.01 (d, 3H, J=6.8 Hz, $CH_3$).

$^{19}$FNMR δ −83.55 (s, $CF_3$), −116.50 (br s, $CF_2$).

MS (CI, $CH_4$) m/z (rel intensity) 675 ($MH^+$, 25), 359 (100), 317(75), 262(28), 230(40), 210(22), 70(52).

Anal. ($C_{31}H_{39}F_5N_4O_7$) C,H,N.

EXAMPLE 2

Preparation of (E)-N-[4-(4-Morpholinylcarbonyl)benzoyl]-L-valyl-N-[3,3,4,4,4-pentafluoro-1-(1-methylethyl)-2-(1-oxopropoxy)-1-butenyl]-L-prolinamide

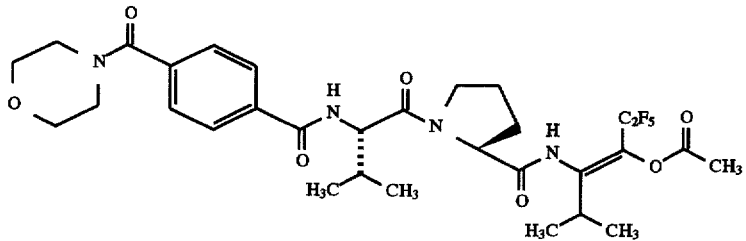

MDL 103,279

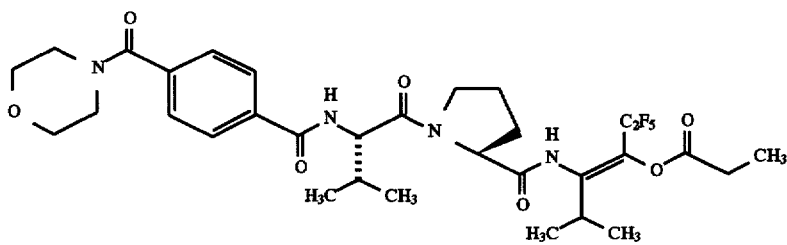

MDL 104,226

Treatment of N-[4-(4-morpholinylcarbonyl)benzoyl]-L-valyl-N-[3,3,4,4,4-pentafluoro-1-(1-methylethyl)-2-oxobutyl]-L-prolinamide with propionic anhydride, using the same general procedure employed in Example 1, and recrystalliztion of the crude product from EtOAc gives MDL 104,226 as a white solid. Yield: 69%, mp 138°–144° C. (dec).

TLC $R_f$ 0.35 (1:9 acetone-EtOAc).

$^1$HNMR δ 8.00 (br s, 1H, NHC=C), 7.88–7.84 (m, 2H, ½ aryl), 7.52–7.46 (m, 2H, ½ aryl), 6.85 (br d, 1H, J=8.8 Hz, NH), 4.87 (dd, 1H, J=6.3, 8.8 Hz, CH), 4.65 (dd, 1H, J=2.6, 8.0 Hz, CH), 3.92–3.53 (m, 8H), 3.40 (br s, 2H), 2.71 (septet, 1H, J=6.9 Hz, CHC=C), 2.52 (q, 2H, J=7.5 Hz, COCH$_2$), 2.50–2.40 (m, 1H), 2.24–1.85 (m, 4H), 1.22 (t, 3H, J=7.5 Hz, CH$_3$), 1.08 (d, 3H, J=6.9 Hz, CH$_3$), 1.07 (d, 3H, J=6.5 Hz, CH$_3$), 1.05 (d, 3H, J=6.8 Hz, CH$_3$), 1.01 (d, 3H, J=6.7 Hz, CH$_3$).

$^{19}$FNMR δ –83.57 (s, CF$_3$), –116.27 and –116.55 (AB quartet, J=280 Hz, CF$_2$).

MS (CI, CH$_4$) m/z (rel intensity) 689 (MH$^+$, 17), 414(20), 373(100), 317(22), 77(54), 75(23), 70(20).

Anal. (C$_{32}$H$_{41}$F$_5$N$_4$O$_7$) C,H,N.

EXAMPLE 3

Preparation of (E)-N-[4-(4-Morpholinylcarbonyl) benzoyl]-L-valyl-N-[3,3,4,4,4-pentafluoro-1-(1-methylethyl)-2-(2-methyl-1-oxopropoxy)-1-butenyl] -L-prolinamide 8.1 Hz, CH), 3.94–3.55 (m, 8H), 3.40 (br s, 2H), 2.74 (septet, 1H, J=7.0 Hz, COCH), 2.68 (septet, 1H, J=6.9 Hz, CHC=C), 2.50–2.40 (m, 1H), 2.25–1.86 (m, 4H), 1.26 (d, 6H, J=7.0 Hz, 2×CH$_3$), 1.09 (d, 3H, J=6.9 Hz, CH$_3$), 1.07 (d, 3H, J=6.8 Hz, CH$_3$), 1.05 (d, 3H, J=6.9 Hz, CH$_3$), 1.01 (d, 3H, J=6.7 Hz, CH$_3$).

$^{19}$FNMR δ –83.68 (s, CF$_3$), –116.16 and –116.66 (AB quartet, J=282 Hz, CF$_2$).

MS (CI, CH$_4$) m/z (rel intensity) 703 (MH$^+$, 20), 387(56), 317(78), 290(28), 230(35), 91(100), 89(80), 71(90), 70(80).

Anal. (C$_{33}$H$_{43}$F$_5$N$_4$O$_7$) C,H,N.

EXAMPLE 4

Preparation of (Z)-N-[4-(4-Morpholinylcarbonyl) benzoyl]-L-valyl-N-[2-(acetyloxy)-3,3,4,4,4-pentafluoro-1-(1-methylethyl)-1-butenyl]-L-prolinamide

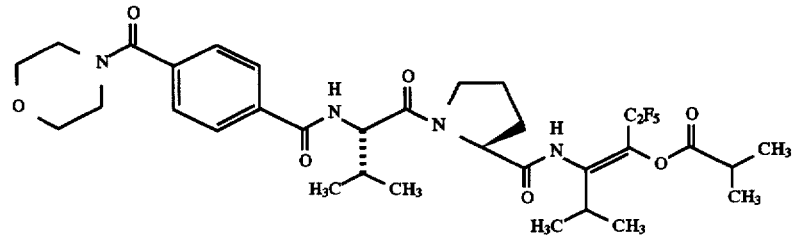

MDL 105,658

Treatment of N-[4-(4-morpholinylcarbonyl)benzoyl]-L-valyl-N-[3,3,4,4,4-pentafluoro-1-(1-methylethyl)-2-oxobutyl]-L-prolinamide with isobutyric anhydride, using the same general procedure employed in Example 1, and recrystalliztion of the crude product from EtOAc gives MDL 105,658 as a white solid. Yield: 54%, mp 135°–142° C. (dec).

TLC $R_f$ 0.34 (1:9 acetone-EtOAc).

$^1$HNMR δ 7.98 (br s, 1H, NHC=C), 7.89–7.84 (m, 2H, ½ aryl), 7.51–7.46 (m, 2H, ½ aryl), 6.87 (br d, 1H, J=8.8 Hz, NH), 4.87 (dd, 1H, J=6.3, 8.8 Hz, CH), 4.65 (dd, 1H, J=2.6,

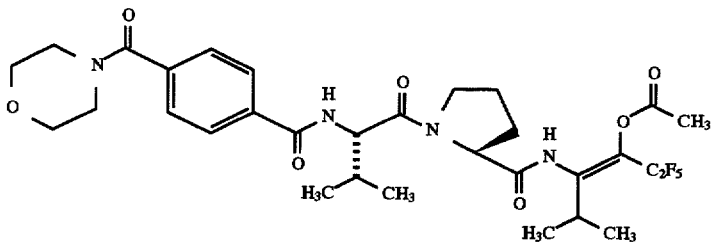

MDL 105,457

To a stirred solution of N-[4-(4-morpholinylcarbonyl)benzoyl]-L-valyl-N-[3,3,4,4,4-pentafluoro-1-(1-methylethyl)-2-oxobutyl]-L-prolinamide (0.50 g, 0.79 mmole), Et₃N (0.16 mL, 1.19 mmole) and 4-dimethylaminopyridine (0.19 g, 1.58 mmole) in CH₂Cl₂ (2 mL) under N₂ atmosphere and heated to reflux, add acetic anhydride (0.22 mL, 2.37 mmole), dropwise. After 30 minutes at reflux, cool the reaction mixture, dilute the reaction mixture with CH₂Cl₂ (45 mL) and wash the reaction mixture with 0.5N aqueous hydrochloric acid (2×35 mL) followed by 25 mL of a mixture of 0.5N aqueous hydrochloric acid-brine (1:9). Drying (MgSO₄) and concentration gives the crude product. Flash chromatography (5×17 cm silica gel column) eluting with ethyl acetate, followed by recrystallization from diethyl ether gives MDL 105,457 as a white solid. Yield: 49 mg (9%) yield.

TLC $R_f$=0.17 (EtOAc).

¹HNMR δ 7.96 (br s, 1H, NHC=C), 7.89–7.83 (m, 2H, ½ aryl), 7.53–7.46 (m, 2H, ½ aryl), 6.78 (br d, 1H, J=8.7 Hz, NH), 4.84 (dd, 1H, J=6.6, 8.8 Hz, CH), 4.61 (dd, 1H, J=2.6, 8.0 Hz, CH), 3.97–3.53 (m, 8H), 3.41 (br s, 2E), 3.13 (septet, 1H, J=6.7 Hz, CHC=C), 2.50–2.39 (m, 1H), 2.20–2.03 and 2.01–1.87 (pr m, 4H), 2.13 (s, 3H, COCH₃), 1.11 (d, 6H, J=6.7 Hz, 2×CH₃), 1.06 (d, 3H, J=6.7 Hz, CH₃), 1.02 (d, 3H, J=6.7 Hz, CH₃).

¹⁹FNMR δ −84.73 (t, J=3 Hz, CF₃), −113.63 (br s, CF₂).

MS (CI, CH₄) m/z (rel intensity) 675 (MH⁺, 17), 635(16), 385(100), 121(30).

EXAMPLE 5

Preparation of (E)-N-[(1,1-Dimethylethoxy)carbonyl]-L-alanyl-L-alanyl-N-[2-(acetyloxy)-3,3,3-trifluoro-1-(1-methylethyl)-1-propenyl]-L-prolinamide (SEQ. ID NO. 2)

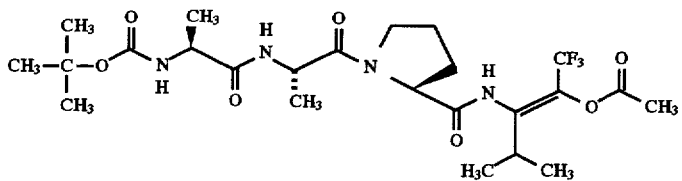

MDL 45,037

Method A: To a stirred solution of N-[(1,1-Dimethylethoxy)carbonyl]-L-alanyl-L-alanyl-N-[3,3,3-trifluoro-1-(1-methylethyl)-2-oxopropyl]-L-prolinamide (1.00 g, 1.97 mmole, EP Pat. Appl. Publ. No. 0195212) in CH₃CN (5 ml) under N₂ atmosphere and cooled to −20° C. (dry ice-CCl₄ bath), is added acetic anhydride (0.56 mL, 5.90 mmole) followed immediately by 4-dimethylaminopyridine (480 mg, 3.93 mmole). After 2 hours at −20° C., the reaction mixture is diluted with CH₂Cl₂ (75 mL) and washed with 0.5N aqueous hydrochloric acid (2×50 mL) followed by 50 mL of a mixture of 0.5N hydrochloric acid-brine (1:9). Drying (MgSO₄) and concentration gives the crude product. Flash chromatography (6×17 cm silica gel column) eluting with ethyl acetate-hexane (85:15) gives MDL 45,037 [0.54 g (50% yield)] as a white solid; mp=111°–114° C. (dec).

TLC $R_f$=0.35 (EtOAc).

¹HNMR δ 8.44 (br s, 1H, NHC=C), 7.88 (br d, 1H, J=6.7 Hz, NH), 5.29 (br d, 1H, J=7.4 Hz, NH), 4.94–4.82 (m, 1H, CH), 4.75 (dd, 1H, J=2.8, 8.0 Hz, CH), 4.61–4.45 (m, 1H, CH), 3.79–3.68 and 3.68–3.57 (pt m, 2H, CH₂N), 2.70 (septet, 1H, J=6.9 Hz, CHC=C), 2.36–1.96 (m, 4H), 2.23 (s, 3H, COCH₃), 1.44 (s, 9H, O-t-Bu), 1.33 (d, 3H, J=6.8 Hz, CH₃), 1.24 (d, 3H, J=6.8 Hz, CH₃), 1.00 (d, 3H, J=6.8 Hz, CH₃), 0.96 (d, 3H, J=6.90 Hz, CH₃).

¹³CNMR δ 172.2, 171.9, 171.2, 167.9, 155.7, 139.9, 132.9 (q, J=35.0 Hz), 119.9 (q, J=274.5 Hz, CF₃), 80.4, 49.5, 47.5, 46.2, 30.2, 28.3, 28.25, 27.9, 24.9, 20.1, 20.02, 19.96, 19.1, 19.0, 18.5.

¹⁹FNMR δ −66.04 (s, CF₃).

IR (CHCl₃ film) 3428, 3293, 2980, 2936, 2878, 1788, 1670, 1630, 1460, 1370, 1333, 1244, 1219, 1179, 1141, 1117, 756 cm⁻¹.

MS (CI, CH₄) m/z (rel intensity) 551 (MH⁺, 38), 495 (100), 453(18), 452(17), 340(17), 309(52), 284(13), 70(19).

Anal. (C₂₄H₃₇F₃N₄O₇) C,H,N.

Method B: To a stirred solution of N-[(1,1-Dimethylethoxy)carbonyl]-L-alanyl-L-alanyl-N-[3,3,3-trifluoro-1-(1-methylethyl)-2-oxopropyl]-L-prolinamide (254 mg, 0.50 mmole, EP Pat. Appl. Publ. No. 0195212) in pyridine (1.25 mL) under N₂ atmosphere and cooled in an ice-water bath is added acetic anhydride (0.47 mL, 5.0 mmole) dropwise. After 26 hours, the reaction mixture is diluted with CH₂Cl₂ (45 mL) and the organics washed with 0.5N aqueous hydrochloric acid (2×30 mL) followed by 40 mL of a mixture of 0.5N aqueous hydrochloric acid-brine (1:9). Drying (MgSO₄) and concentration gives crude product [0.32 g, 91% (E)-enol acetate, <3% starting material, 3% (Z)-enol acetate by ¹⁹FNMR]. Flash chromatography (3×16 cm silica gel column) eluting with ethyl acetate-hexane (4:1) gives MDL 45,037.

The intermediates of the title compounds of examples 6–8, wherein the CFR₃R₄ substituent is —CF₃, may all be synthesized from the processes of scheme L.

Scheme L
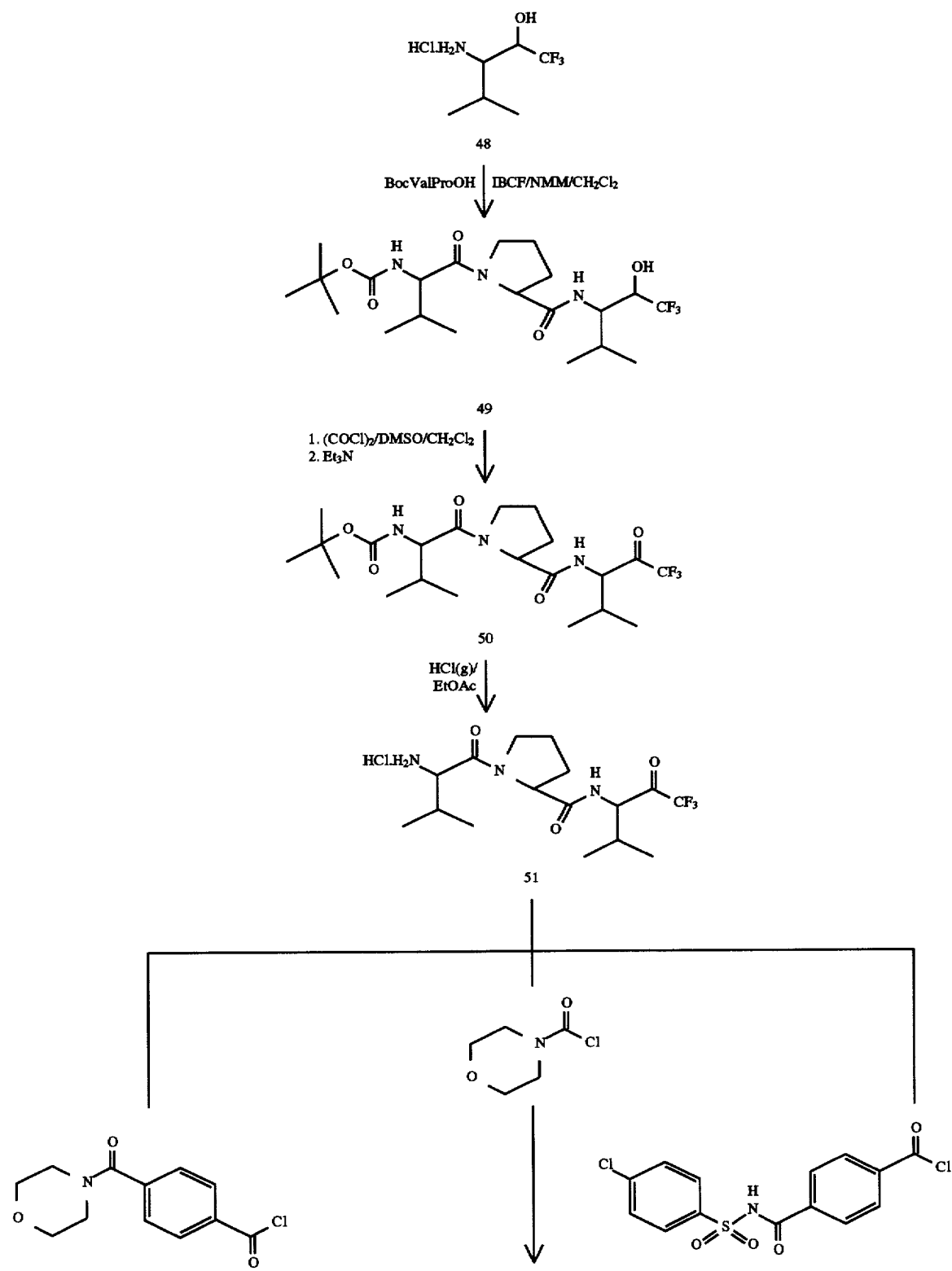

-continued
Scheme L

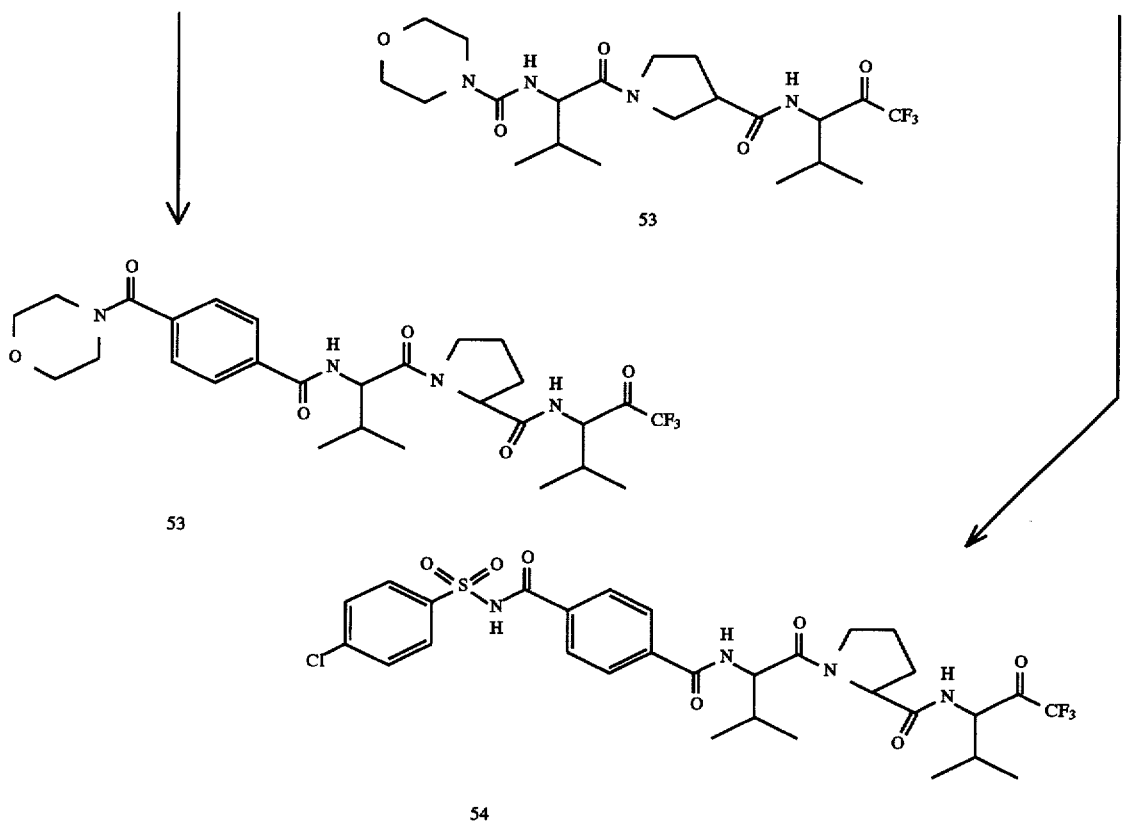

EXAMPLE 6

Preparation of (E)-N-[4-(4-Morpholinylcarbonyl) benzoyl]-L-valyl-N-[2-(acetyloxy)-3,3,3-trifluoro-1-(1-methylethyl)-1-propenyl]-L-prolinamide aqueous layer is extracted with additional $CH_2Cl_2$ (100 mL) and the combined organic extracts are washed with 0.5N aqueous hydrochloric acid, saturated aqueous $NaHCO_3$ (2×200 mL) and brine (125 mL). Drying ($MgSO_4$) and concentration gives crude 49. Trituration with $Et_2O$-hexane

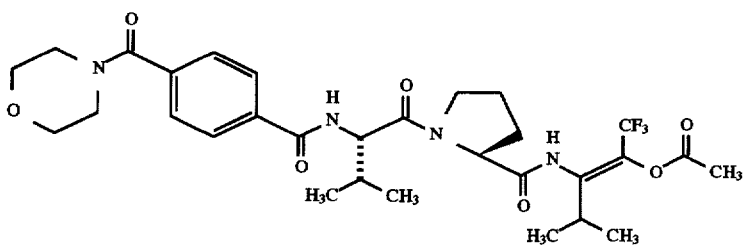

MDL 103,467

Step a: N-[(1,1-Dimethylethoxy)carbonyl]-L-valyl-N-[3,3,3-trifluoro-2-hydroxy-1-(1-methylethyl) propyl]-L-prolinamide (49)

To a stirred solution of Boc-L-Val-L-Pro-OH (2.00 g, 6.36 mmol) in $CH_3CN$ (85 mL) under nitrogen atmosphere and cooled to −18° C. is added NMM (0.70 mL, 6.36 mmol) followed by IBCF (0.83 mL, 6.36 mmol). After 15 min, add a light suspension of 48 (a single pair of enantiomers, 1.78 g, 6.36 mmol) and NMM (0.70 mL, 6.36 mmol) in $CH_3CN$ (25 mL). Stir for 3 hours and then allow the reaction mixture to warm to room temperature. Concentrate the reaction mixture and partition the residue between $CH_2Cl_2$ (400 mL) and 0.5N aqueous hydrochloric acid (200 mL). The acidic and filtration gives 49 (2.41 g (81%), mixture of two diastereomers, ratio≈1:1) as an off-white solid.

$^1$HNMR (DMSO-$d_6$) δ 7.70 (br d, 0.5H, NH), 7.39 (br d, 0.5H, NH), 6.77 (br d, 0.5H, NH), 6.71 (br d, 0.5H, NH), 6.39 (d, 0.5H, OH), 6.36 (d, 0.5H, OH), 4.40–4.26 (m, 1H, CH), 4.09–3.94 (m, 2H), 3.94–3.46 (m, 3H), 2.20–1.60 (m, 6H), 1.37 (s, 9H, tBu), 0.98–0.72 (m, 12H, 4×$CH_3$).

$^{19}$FNMR δ −74.04 (d, J=6.8 Hz, $CF_3$, diastereomer A), −74.14 (d, J=6.8 Hz, $CF_3$, diastereomer B).

MS (DCI, $CH_4$) m/z (rel intensity) 468 ($MH^+$, 40), 412 (92), 368 (100).

Anal. ($C_{21}H_{36}F_3N_3O_5$) C,H,N.

Step b: N-[(1,1-Dimethylethoxy)carbonyl]-L-valyl-N-[3,3,3-trifluro-1-(1-methylethyl)-2-oxopropyl]-L-prolinamide (50)

To a stirred solution of oxalyl chloride (0.31 mL, 3.56 mmol) in CH$_2$Cl$_2$ (30 mL) cooled to –60° C. is added DMSO (0.51 mL, 7.12 mmol) dropwise. After 6 min, a solution of 49 (1.11 g, 2.37 mmol) in a mixture of CH$_2$Cl$_2$ (5 mL) and DMSO (3 mL) is slowly added and, 20 min later, Et$_3$N (1.99 mL, 14.25 mmol) is added. The reaction mixture is allowed to warm to room temperature, diluted with CH$_2$Cl$_2$ (100 mL) and washed with 0.5N aqueous HCl (2×150 mL), and half-saturated aqueous NaHCO$_3$ (2×100 mL) followed by brine (75 mL). Drying (MgSO$_4$) and concentration gives 50 (1.06 g, 96%, mixture of two diastereomers, ratio≈1:1) as a white foam.

$^1$HNMR δ 7.98 (br d, 0.5H, NH), 7.61 (br d, 0.5H, NH), 5.23 (d, 1H, NH), 4.87–4.79 (m, 1H, CH), 4.74 (dd, 0.5H, CH), 4.64 (dd, 0.5H, CH), 4.36–4.24 (m, 1H, CH), 3.82–3.68 and 3.65–3.54 (pr m, 2H, CH$_2$N), 2.57–1.76 (m, 6H, CH$_2$CH$_2$ and 2×CH), 1.42 (s, 9H, tBu), 1.10–0.87 (m, 12H, 4×CH$_3$).

$^{19}$FNMR δ –76.94 (s, CF$_3$, diastereomer A), –77.00 (s, CF$_3$, diastereomer B).

MS (DCI, CH$_4$) m/z (rel intensity) 466 (MH$^+$, 58), 410 (100), 390 (17), 366 (17).

HRMS (C$_{21}$H$_{35}$F$_3$N$_3$O$_5$)(MH$^+$) calcd 466.2529, obsd 466.2507.

Step c: N-L-valyl-N-[3,3,3-trifluro-1-(1-methylethyl)-2-oxopropyl]-L-prolinamide, Hydrochloride Salt (51)

A stirred solution of 50 (1.19 g, 2.56 mmol) is cooled to 0° C. and treated with HCl gas until saturation. The mixture is stirred at 0° C. for 30 min and the solvent is removed in vacuo to give 51 (1.0 g, 97%, mixture of 2 diastereomers of ketone form and 2 diastereomers of hydrate form, 3:1 ratio of diastereomers and 4:1 ratio of hydrate to ketone) as a white solid.

$^1$HNMR (DMSO-d$_6$) δ 8.80 (d, J=7.15 Hz, 0.1H, NH), 8.73 (d, J=7.15 Hz, 0.2H, NH), 8.14 (bs, 5H), 7.69 (d, J=10.2 Hz, 1H, NH), 7.52 (d, J=10.2 Hz, 0.2H, NH), 6.93 (s, 0.3H, OH), 6.90 (s, 0.7H, NH), 6.84 (s, 0.7H, NH), 6.79 (s, 0.3H, NH), 4.75 (series of m, 2H), 4.04–3.91 (series of m, 3H), 3.73 (m, 2H), 3.47 (m, 2H), 2.34–1.66 (series of m, 6H, 2×β-CH of Val and CH$_2$CH$_2$), 1.06–0.77 (m, 12H, 4×CH$_3$).

$^{19}$FNMR (DMSO-d$_6$) δ –74.84 (s, COCF$_3$), –74.98 (s, COCF$_3$), –80.88 [s, C(OH)$_2$CF$_3$], –81.10 [s, C(OH)$_2$CF$_3$].

IR (KBr pellet) 3431, 2970, 1647, 1595, 1506, 1471, 1172 cm$^{-1}$.

MS (DCI, CH$_4$) m/z (rel intensity) 366 (MH$^+$, 100), 267 (48), 197 (20), 169 (25).

HRMS (C$_{16}$H$_{27}$F$_3$N$_3$O$_3$) (MH$^+$ free amine) calcd 366.2005, obsd 366.1995.

Step d: N-[4-(4-Morpholinylcarbonyl)benzoyl]-L-valyl-N-[3,3,3-trifluro-1-(1-methylethyl)-2-oxopropyl]-L-prolinamide (52)

To a stirred suspension of 4-(4-morpholinylcarbonyl)benzoic acid (1.10 g, 4.68 mmol) in 1,2-dichloroethane (10 mL) is added benzyltriethylammonium chloride (5 mg) and thionyl chloride (4.80 mmol, 0.35 mL) and the mixture is heated to reflux. After 2 hours, cool the reaction solution to room temperature and concentrate in vacuo to give the acid chloride. The acid chloride is dissolved in CH$_2$Cl$_2$ (10 mL) and added to a solution of 51 (1.00 g, 2.49 mmol) and NMM (0.82 mL, 7.50 mmol) in CH$_2$Cl$_2$ (10 mL). Stir for 3 hours, dilute with CH$_2$Cl$_2$ (50 mL) and wash with 0.5N aqueous hydrochloric acid (2×40 mL), saturated aqueous NaHCO$_3$ (2×40 mL) and brine (25 mL). Drying (MgSO$_4$) and concentration gives crude 52. Purification by flash chromatograpy (1:19, acetone:EtOAc) gives 52 (2:1::LLL:LLD) as a white foam. Yield=1.20 g (82%).

$^1$HNMR δ 7.85 (d, J=8.0 Hz, 2H, aryl), 7.76 (d, J=7.0 Hz, 0.33H, NH), 7.47 (d, J=8.0 Hz, 2H, aryl), 7.34 (d, J=7.5 Hz, 0.66H, NH), 6.80 (d, J=8.6 Hz, 1H, NH), 4.86 (m, 2H), 4.70 (dd, J=8.0, 2.13 Hz, 0.33H, CH of Pro), 4.61 (dd, J=8.3, 3.1 Hz, 0.66H, CH of Pro), 3.91–3.35 (m, 10H), 2.53–1.80 (series of m, 6H, 2×β-CH of Val and CH$_2$CH$_2$), 1.12–0.88 (m, 12H, 4×CH$_3$).

$^{19}$FNMR δ –76.89 (s, CF$_3$), –76.96 (s, CF$_3$).

MS (DCI, CH$_4$) m/z (rel intensity) 583 (MH$^+$, 20), 317 (10), 267 (100).

HRMS (C$_{28}$H$_{38}$F$_3$N$_4$O$_6$) (MH$^+$) calcd 583.2793, obsd 583.2765.

Step e: (E)-N-[4-(4-Morpholinylcarbonyl)benzoyl]-L-valyl-N-[2-(acetyloxy)-3,3,3-trifluro-1-(1-methylethyl)-1-propenyl]-L-prolinamide (MDL 103,467)

Treatment of 52 with acetic anhydride, according to the general procedure of Example 5, Method A, followed by flash chromatography [eluting with acetone-ethyl acetate (1:9)] and recrystallization from ethyl acetate-hexane gives MDL 103,467 (38% yield, mp 121°–129° C.) as fine white needles.

TLC R$_f$ 0.34 (15:85 acetone-EtOAc).

$^1$HNMR δ 8.01 (br s, 1H, NHC=C), 7.89–7.84 (m, 2H, ½ aryl), 7.51–7.46 (m, 2H, ½ aryl), 6.83 (br d, 1H, J=8.8 Hz, NH), 4.87 (dd, 1H, J=6.3, 8.7 Hz, CH), 4.67 (dd, 1H, J=2.4, 8.0 Hz, CH), 3.93–3.52 (m, 8H), 3.40 (br s, 2H), 2.72 (septet, 1H, J=6.9 Hz, CHC=C), 2.55–2.45 (m, 1H), 2.25 (s, 3H, COCH$_3$), 2.23–2.02 (m, 3H), 1.99–1.85 (m, 1H), 1.07 (d, 3H, J=6.9 Hz, CH$_3$), 1.06 (d, 3H, J=6.9 Hz, CH$_3$), 1.05 (d, 3H, J=6.9 Hz, CH$_3$), 1.01 (d, 3H, J=6.7 Hz, CH$_3$).

$^{19}$FNMR δ –67.30 (s, CF$_3$).

MS (CI, CH$_4$) m/z (rel intensity) 625 (MH$^+$, 90), 414(17), 309(100), 86(35), 85(38).

Anal. (C$_{30}$H$_{39}$F$_3$N$_4$O$_7$) C,H,N.

EXAMPLE 7

Preparation of (E)-N-(4-Morpholinylcarbonyl)-L-valyl-N-[2-(acetyloxy)-3,3,3-trifluoro-1-(1-methylethyl)-1-propenyl]-L-prolinamide

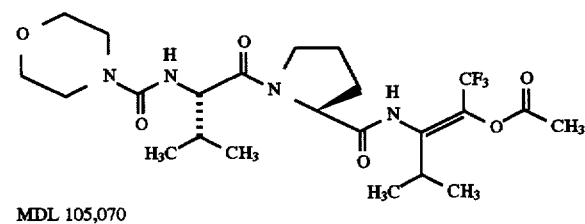

MDL 105,070

Step a: N-(4-Morpholinylcarbonyl)-L-valyl-N-[3,3,3-trifluoro-1-(1-methylethyl)-2-oxopropyl]-L-prolinamide (53)

To a stirred solution of 51 (430 mg, 1.07 mmol) in CH$_2$Cl$_2$ (35 mL) under argon is added NMM (0.24 mL, 2.14 mmol)

followed immediately by 4-morpholinecarbonyl chloride (0.50 mL, 4.28 mmol). After 2.5 hours, the reaction mixture is concentrated to give crude 53. Purification by flash chromatography (20:80::acetone:EtOAc) gives 53 (240 mg, 47%, mixture of 2 diastereomers of ketone form and 2 diastereomers of hydrate form, ratio≅9:9:1:1, respectively) as a white solid.

$^{19}$FNMR δ −76.94 (s, COCF$_3$), −77.01 (s, COCF$_3$), −82.51 [s, C(OH)$_2$CF$_3$], −83.04 [s, C(OH)$_2$CF$_3$].

MS (DCI, CH$_4$) m/z (rel intensity) 479 (MH$^+$, 62), 267(43), 213(100), 185(22).

HRMS (C$_{21}$H$_{33}$F$_3$N$_4$O$_5$) (M$^+$) calcd 478.2403, obsd 478.2401.

Step b: (E)-N-(4-Morpholinylcarbonyl)-L-valyl-N-[2-(acetyloxy)-3,3,3-trifluoro-1-(1-methylethyl)-1-propenyl]-L-prolinamide (MDL 105,070)

Treatment of 53 with acetic anhydride, according to the general procedure of Example 5, Method A, followed by flash chromatography [eluting with acetone-ethyl acetate (1:9)] gives MDL 105,070 (6% yield) as a white solid.

TLC R$_f$ 0.33 (15:85 acetone-EtOAc).

$^1$HNMR δ 8.12 (br s, 1H, NHC=C), 5.12 (br d, 1H, J=8.5 Hz, NH), 4.68 (dd, 1H, J=1.6, 7.7 Hz, CH), 4.52 (dd, 1H, J=6.5, 8.5 Hz, NH), 3.92–3.79 (m, 1H, ½ CH$_2$N), 3.75–3.59 (m, 5H, ½ CH$_2$N and CH$_2$OCH$_2$), 3.49–3.31 (m, 4H, CH$_2$NCH$_2$), 2.71 (septet, 1H, J=6.9 Hz, CHC=C), 2.55–2.43 (m, 1H), 2.25 (s, 3H, COCH$_3$), 2.16–1.81 (m, 4H), 1.05 (d, 3H, J=6.8 Hz, CH$_3$), 1.04 (d, 3H, J=7.0 Hz, CH$_3$), 1.01 (d, 3H, J=6.8 Hz, CH$_3$), 0.96 (d, 3H, J=6.6 Hz, CH$_3$).

$^{19}$FNMR δ −67.33 (s, CF$_3$).

MS (CI, CH$_4$) m/z (rel intensity) 521 (MH$^+$, 59), 501(10), 461(17), 337(10), 309(68), 213(100), 185(22), 114(10), 85(10), 84(15), 70(12).

HRMS (C$_{23}$H$_{36}$F$_3$N$_4$O$_6$) (MH$^+$) calcd 521.2587, obsd 521.2603.

EXAMPLE 8

Preparation of (E)-N-[4-[(4-Chlorophenyl)sulfonylaminocarbonyl]benzoyl]-L-valyl-N-[2-(acetyloxy)-3,3,3-trifluoro-1-(1-methylethyl)-1-propenyl]-L-prolinamide Method A; step a: N-[4-[(4-Chlorophenyl)sulfonylaminocarbonyl]benzoyl]-L-valyl-N-[3,3,3-trifluoro-1-(1-methylethyl)-2-oxopropyl]-L-prolinamide (54)

To a stirred light suspension of 4-[(4-chlorophenyl)sulfonylaminocarbonyl]benzoic acid (0.68 g, 2.02 mmol; EP Pat. Appl. Publ. No. 0189305 B1) in CH$_2$Cl$_2$ (18 mL) and DMF (2 mL) under argon is added oxalyl chloride (0.18 mL, 2.02 mmol) dropwise. After 50 minutes, add a solution of 51 (0.81 g, 2.02 mmol) and NMM (1.00 mL, 9.07 mmol) in CH$_2$Cl$_2$ (8 mL). Stir for 3 hours and then pour the reaction mixture into H$_2$O (75 mL) and separate the layers. The aqueous phase is extracted with additional EtOAc (2×35 mL) and the combined organic extracts are washed with 1N aqueous hydrochloric acid (2×30 mL) followed by brine (30 mL). Drying (MgSO$_4$) and concentration gives crude 54. Purification by flash chromatography [gradient (54–74%) of EtOAc in hexane containing 1% acetic acid] gives 54 [0.96 g (70%), (1:1::LLL:LLD)] as a white solid foam.

$^1$HNMR δ 10.40 (br s, 1H, SO$_2$NH), 8.11–8.03 and 7.79–7.71 and 7.68–7.60 and 7.56–7.49 (four m, 8H, 2×Ar), 7.28–7.13 (m, 2H, 2×NH), 4.97–4.84 (m, 2H, 2×CH), 4.67 (dd, 0.5H, α-CH), 4.59 (dd, 0.5H, α-CH), 3.99–3.86 and 3.77–3.61 (pr m, 2H, CH$_2$N), 2.47–1.83 (m, 6H), 1.14–0.81 (m, 12H, 4×CH$_3$).

$^{19}$FNMR δ −76.89 (s, CF$_3$, diastereomer A), −76.97 (s, CF$_3$, diastereomer B).

MS (DCI, CH$_4$) m/z (rel intensity) 687 (MH$^+$, 38), 267 (100), 249 (45), 247 (58).

HRMS (C$_{30}$H$_{35}$ClF$_3$N$_4$O$_7$S) (MH$^+$) calcd 687.1867, obsd 687.1841.

Step b: (E)-N-[4-[(4-Chlorophenyl)sulfonylaminocarbonyl]benzoyl]-L-valyl-N-[2-(acetyloxy)-3,3,3-trifluoro-1-(1-methylethyl)-1-propenyl]-L-prolinamide (MDL 105,928)

Treatment of 54 with acetic anhydride, according to the general procedure of Example 5, Method A, followed by flash chromatography [eluting with a gradient (0–0.5%) of acetic acid in EtOAc] gives the title compound of Example 8.

Method B: Treatment of 54 with acetic anhydride, according to the alternative general procedure of Example 5, Method B, followed by flash chromatography [eluting with a gradient (0–0.5%) of acetic acid in ethyl acetate] gives a 49% yield of the title compound of Example 8.

TLC R$_f$ 0.38 (0.5:99.5 acetic acid-EtOAc)

$^1$HNMR δ 10.08 (br s, 1H, NHSO$_2$), 8.06 (d, 2H, J=8.0 Hz, aryl), 7.87 (br s, 1H, NHC=C), 7.77 (d, 2H, J=7.8 Hz, aryl), 7.65 (d, 2H, J=7.8 Hz, aryl), 7.51 (d, 2H, J=8.0 Hz, aryl), 7.05 (br d, 1H, J=7.3 Hz, NH), 4.92 (dd, 1H, J=6.7, 7.8 Hz, CH), 4.65 (dd, 1H, J=1.8, 7.3 Hz, CH), 3.96–3.83 (m, 1H, ½ CH$_2$N), 3.76–3.65 (m, 1H, ½ CH$_2$N), 2.71 (septet, 1H, J=6.8 Hz, CHC=C), 2.46–2.34 (m, 1H), 2.25 (s, 3H, COCH$_3$), 2.25–1.89 (m), 1.07 (d, 3H, J=6.7 Hz, CH$_3$), 1.03 (d, 3H, J=6.8 Hz, CH$_3$), 1.01 (d, 3H, J=6.8 Hz, CH$_3$), 0.99 (d, 3H, J=6.9 Hz, CH$_3$).

$^{19}$FNMR δ −67.00 (s, CF$_3$).

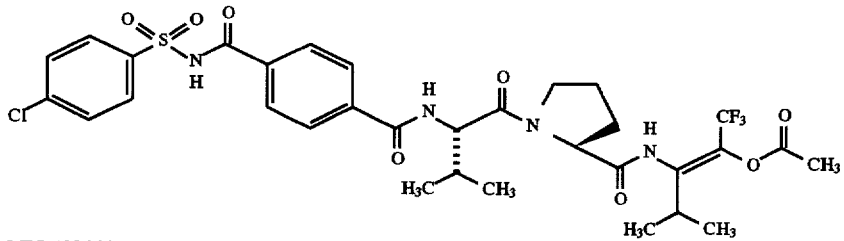

MDL 105,928

MS (CI, CH$_4$) m/z (rel intensity) 729 (MH$^+$, 100), 709 (10), 669 (13), 518 (25), 309 (100), 212 (10), 70 (28).

Anal. (C$_{32}$H$_{36}$ClF$_3$N$_4$O$_8$S.1H$_2$O)C,H,N.

EXAMPLE 9

Alternative Preparation of Boc-Val-CF$_2$CF$_3$

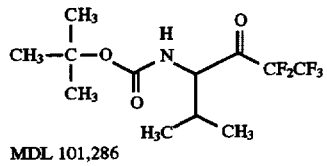

MDL 101,286

A mixture of 288.0 g (1.11 mol) of Boc-Val N-methyl-O-methyl hydroxamic acid and 4.7 L of anhydrous Et$_2$O was charged to a 12-L 3-necked flask fitted with a stirrer, thermometer, dry ice condenser, gas dispersion tube and continuous N$_2$ purge. The resulting solution was cooled to –60° C. to –65° C. A total of 885.2 g (3.60 mol) of C$_2$F$_5$I was added via a gas dispersion tube over about 30 min to the solution of Boc-Val N-methyl-O-methyl hydroxamic acid while maintaining a temperature of about –65° C. Immediately upon completing the gas addition, a total of 2.39 L of 1.5M CH$_3$Li.LiBr in Et$_2$O (3.59 mol) was added over 1 h maintaining a reaction temperature of –52° C. to –58° C. A precipitate formed after about ⅓ of the CH$_3$Li.LiBr had been added but a complete solution was present at the end of the addition. The resulting solution was stirred at –52° C. to –58° C. for 1 h. The reaction was monitored by GC (R$_t$ of MDL 101,286=1.3 min, R$_t$ of Boc-Val N-methyl-O-methyl hydroxamic acid=5.1 min) and found to contain 7.2% of Boc-Val N-methyl-O-methyl hydroxamic acid. A total of 255 mL (3.47 mol) of acetone was added over about 15 min maintaining a reaction temperature of –52° C. to –58° C. and the resulting mixture was stirred for 10 min. The mixture was quenched into a 22 L flask containing 4.7 L of 0.75M KHSO$_4$ which had been cooled to about 0° C. The organic layer was separated and washed with 3 L of H$_2$O. The organic layer was dried using 500 g of MgSO$_4$ and filtered to remove the drying agent. The filtrate was concentrated at 40° C./100 torr to a semi-solid weighing 409 g. The crude material was dissolved in 1.2 L of hexane at 45° C. and cooled slowly over about 30 min to –25° C. to –30° C. The solid which crystallized was filtered off and washed with 250 mL of hexane at –30° C. The MDL 101,286 obtained was vacuum dried (25° C./100 torr) to give 176.7 g. The filtrate was concentrated at 35° C./100 torr to a residue weighing 153.5 g. The material was put on a Kugelrohr distillation apparatus and a forerun was collected up to 40° C./0.6 torr. The receiver was changed and a total of 100.5 g of crude MDL 101,286 was collected at 40° C.–60° C./0.6 torr. The crude product was dissolved in 500 mL of hexane at about 50° C. The resulting solution was cooled to –30° C. The solid which crystallized was filtered off and washed with 100 mL of cold (–30° C.) hexane. The product was vacuum dried at 25° C./100 torr to give another 68.0 g of MDL 101,286 for a total yield of 244.7 g (70% yield) which was 99.9% pure by GC.

Anal. Calcd. for C$_{12}$H$_{18}$F$_5$NO$_3$ (319.28): C, 45.14, H, 5.68, N, 4.39; Found: C, 45.30, 45.49, H, 5.50, 5.58, N, 4.26, 4.35.

In a further embodiment, the present invention provides a method for the treatment of a patient afflicted with a neutrophil associated inflammatory disease comprising the administration thereto of a therapeutically effective amount of a compound of formula I. The term "neutrophil associated inflammatory disease" refers to diseases or conditions characterized by the migration of neutrophils to the site of inflammation and its participation in proteolytic degradation of biological matrices. Neutrophil associated inflammatory diseases for which treatment with a compound of formula I will be particularly useful include: emphysema, cystic fibrosis, adult respiratory distress syndrome, septicemia, disseminated intravascular coagulation, gout, rheumatoid arthritis, chronic bronchitis and inflammatory bowel disease. Compounds of formula I which are particularly preferred for the treatment of neutrophil associated inflammatory diseases include:

(E)-N-[4-(4-morpholinylcarbonyl)benzoyl]-L-valyl-N-[2-(acetyloxy)-3,3,4,4,4-pentafluoro-1-(1-methylethyl)-1-butenyl]-L-prolinamide (E)-N-[4-(4-morpholinylcarbonyl)benzoyl]-L-valyl-N-3,3,4,4,4-pentafluoro-1-(1-methylethyl)-2-(1-oxopropoxy)-1-butenyl]-L-prolinamide (E)-N-[4-(4-morpholinylcarbonyl)benzoyl]-L-valyl-N-[3,3,4,4,4-pentafluoro-1-(1-methylethyl)-2-(2-methyl-1-oxopropoxy)-1-butenyl]-L-prolinamide (Z)-N-[4-(4-morpholinylcarbonyl)benzoyl]-L-valyl-N-[2-(acetyloxy)-3,3,4,4,4-pentafluoro-1-(1-methylethyl)-1-butenyl]-L-prolinamide (E)-N-[(1,1-dimethylethoxy)carbonyl]-L-alanyl-L-alanyl-N-[2-(acetyloxy)-3,3,3-trifluoro-1-(1-methylethyl)-1-propenyl]-L-prolinamide (E)-N-[4-(4-morpholinylcarbonyl)benzoyl]-L-valyl-N-[2-(acetyloxy)-3,3,3-trifluoro-1-(1-methylethyl)-1-propenyl]-L-prolinamide (E)-N-(4-morpholinylcarbonyl)-L-valyl-N-[2-(acetyloxy)-3,3,3-trifluoro-1-(1-methylethyl)-1-propenyl]-L-prolinamide (E)-N-[4-[(4-chlorophenyl)sulfonylaminocarbonyl]benzoyl]-L-valyl-N-[2-(acetyloxy)-3,3,3-trifluoro-1-(1-methylethyl)-1-propenyl]-L-prolinamide.

As used herein, the term "patient" refers to a warm blooded animal such as a mammal which is afflicted with a particular inflammatory disease state. It is understood that guinea pigs, dogs, cats, rats, mice, horses, cattle, sheep, and humans are examples of animals within the scope of the meaning of the term.

The term "therapeutically effective amount" refers to an amount which is effective, upon single or multiple dose administration to the patient, in providing relief of symptoms associated with neutrophil associated inflammatory diseases. As used herein, "relief of symptoms" of a respiratory disease refers to a decrease in severity over that expected in the absence of treatment and does not necessarily indicate a total elimination or cure of the disease. In determining the therapeutically effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective amount of a compound of formula I is expected to vary from about 0.1 milligram per kilogram of body weight per day (mg/kg/day) to about 100 mg/kg/day. Preferred amounts are expected to vary from about 0.5 to about 10 mg/kg/day.

The compounds of this invention are prodrugs of highly potent inhibitors of elastase, particularly human neutrophil elastase or are inhibitors of elastase in their own right. It is believed that the compounds of this invention exert their inhibitory effect through inhibition of the enzyme elastase and thereby provide relief for elastase-mediated diseases including but not limited to emphysema, cystic fibrosis, adult rspiratory distress syndrome, septicemia, disseminated intravascular coagulation, gout, rheumatoid arthritis, chronic bronchitis and inflammatory bowel disease. However, it is understood that the present invention is not limited by any particular theory or proposed mechanism to explain its effectiveness in an end-use application.

In effecting treatment of a patient afflicted with a disease state described above, a compound of formula I can be administered in any form or mode which makes the compound bioavailable in effective amounts, including oral, aerosol, and parenteral routes. For example, compounds of formula I can be administered orally, by aerosolization, subcutaneously, intramuscularly, intravenously, transdermally, intranasally, rectally, topically, and the like. Oral or aerosol administration is generally preferred. One skilled in the art of preparing formulations can readily select the proper form and mode of administration depending upon the particular characteristics of the compound selected the disease state to be treated, the stage of the disease, and other relevant circumstances. Remington's Pharmaceutical Sciences, 18th Edition, Mack Publishing Co. (1990).

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable salts, such as for example, acid addition salts, for purposes of stability, convenience of crystallization, increased solubility and the like.

In another embodiment, the present invention provides compositions comprising a compound of formula I in admixture or otherwise in association with one or more inert carriers. These compositions are useful, for example, as assay standards, as convenient means of making bulk shipments, or as pharmaceutical compositions. An assayable amount of a compound of formula I is an amount which is readily measurable by standard assay procedures and techniques as are well known and appreciated by those skilled in the art. Assayable amounts of a compound of formula I will generally vary from about 0.001% to about 75% of the composition by weight. Inert carriers can be any material which does not degrade or otherwise covalently react with a compound of formula I. Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of formula I in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, parenteral, or topical use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The compounds of formula I of the present invention may also be administered by aerosol. The term aerosol is used to denote a variety of systems ranging from those of colloidal nature to systems consisting of pressurized packages. Delivery may be by a liquified or compressed gas or by a suitable pump system which dispenses the active ingredients. Aerosols of compounds of formula 1 may be delivered in single phase, bi-phasic, or tri-phasic systems in order to deliver the active ingredient. Delivery of the aerosol includes the necessary container, activators, valves, subcontainers, and the like. Preferred aerosol are able to be determined by one skilled in the art.

The compounds of formula I of this invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula 1 or its pharmaceutical salt from about 0.1 to about 10% w/v (weight per unit volume).

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

In vivo, the compounds of formula 1 are believed to be converted by esterases to compounds known to be active as human elastase inhibitors. For example, compounds of formula 1 are converted into compounds disclosed in European Pat. Appl. OPI No. 0410411, published Jan. 30, 1991; European Pat. Appl. OPI No. 0195212, published Sep. 24, 1986; European Pat. Appl. OPI No. 0529568, published Mar. 3, 1993, said references herein disclosed by reference as if fully set forth. The following examples illustrate the extent of elastase inhibition by selected compounds of Formula 1.

EXAMPLE 10

In vitro Assay of Human Neutrophil Elastase in the Presence of MDL 103,279 and Porcine Liver Esterase Human neutrophil elastase was assayed in vitro using N-MeOSuc-Ala-Ala-Pro-Val-p-nitroanilide, available commercially, as substrate. The assay techniques are similar to those described by Mehdi, et al., *Biochemical and Biophysical Research Communications*, 166, 595 (1990). The assay mixture consisted of partially purified elastase and substrate (0.2 mM) in 0.1M HEPES (pH 7.5), 0.5M NaCl, 10% DMSO and 0.1% Brij 35. The reaction (3.0 mL, in a plastic cuvette) was maintained at 37° C. and the hydrolysis of the substrate was followed in the presence of 66 nM of MDL 103,279 and 12.5 units of porcine liver esterase (Sigma Chemical Co., cat. no. E-3128). Enzyme was isolated from human sputum, although recently it has become commercially available. The time course of the reaction was followed for 60 min. The extent of inhibition of elastase progressively increased with time with a half-time of approximately 10 min. From the final rate, a $K_i$ of 25 nM was calculated for the final inhibitory species, presumed to be MDL 101,146 (as disclosed in European Pat. Appl. OPI No. 0529568, published Mar. 3, 1993). This is consistent with the $K_i$ obtained independently for MDL 101,146. The $K_i$ for MDL 103,279, the prodrug, was estimated from the initial rate to be greater than 2 μM. To rule out interference of the esterase with the elastase assay, or a significant spontaneous (i.e. non-enzymatic) hydrolysis rate of MDL 103,279, the following control experiments, as portrayed in FIG. 1, were performed: (A) elastase+elastase substrate; (B) elastase+elastase substrate+porcine liver esterase; (C) elastase+elastase substrate+MDL 103,279; as well as (D) elastase+elastase substrate+esterase+MDL 103,279.

EXAMPLE 11

In vitro Assay of Human Neutrophil Elastase in the Presence of MDL 104,226 and Porcine Liver Esterase Human neutrophil elastase was assayed in vitro in the presence of MDL 104,226 and the techniques and procedures described in Example 10. The use of MDL 104,226 resulted in the same time course, as is evidenced in FIG. 2, line 4, and a final $K_i$ of 25 nM.

EXAMPLE 12

In vitro Assay of Human Neutrophil Elastase in the Presence of MDL 105,658 and Porcine Liver Esterase Human neutrophil elastase was assayed in vitro using MDL 105,658 and the techniques and procedures described in Example 10. The use of MDL 105,658 resulted in the same time course, as is evidenced in FIG. 2, line 6, and final $K_i$ ($K_i$=25 nM) as described above for MDL 103,279.

EXAMPLE 13

In vitro Assay of Human Neutrophil Elastase in the Presence of MDL 105,457 and Porcine Liver Esterase Human neutrophil elastase was assayed in vitro using MDL 105,457 and the techniques and procedures described in Example 10. The use of MDL 105,457 resulted in an onset of inhibition of elastase which was significantly slower than that observed with MDL 103,279, as is evidenced in FIG. 2, line 3.

EXAMPLE 14

In vitro Assay of Human Neutrophil Elastase in the Presence of MDL 103,467 and Porcine Liver Esterase Human neutrophil elastase was assayed in vitro using 133 nM of MDL 103,467 and the techniques and procedures described in Example 10. Upon complete hydrolysis, the $K_i$ determined from the final rate was 16 nM [compared with 12 nM, the $K_i$ of the parent drug, N-[4-(4-Morpholinylcarbonyl)benzoyl]-L-valyl-N-[3,3,3-trifluro-1-(1-methylethyl)-2-oxopropyl]-L-prolinamide 52, determined independently].

EXAMPLE 15

In vitro Assay of Human Neutrophil Elastase in the Presence of MDL 105,070 and Porcine Liver Esterase Human neutrophil elastase was assayed in vitro using 1.67 μM of MDL 105,070 and the techniques and procedures described in Example 10. Upon complete hydrolysis, the $K_i$ determined from the final rate was 150 nM [compared with 190 nM, the $K_i$ for the final product of the parent drug, N-(4-Morpholinylcarbonyl)-L-valyl-N-[3,3,3-trifluoro-1-(1-methylethyl)-2-oxopropyl]-L-prolinamide 53, determined independently].

---

What is claimed is:

1. A compound of the formula

K-P$_4$-P$_3$-P$_2$-EAC    (SEQ. ID NO. 1)

wherein

EAC is a group of the formulae wherein

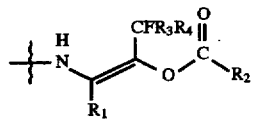

or

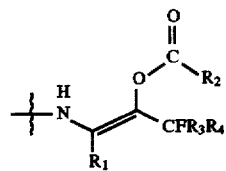

R$_1$ is —CH$_3$, —CH(CH$_3$)$_2$, —CH$_2$CH$_2$CH$_3$, —CH$_2$CH(CH$_3$)$_2$ or —CH(CH$_3$)CH$_2$CH$_3$;

R$_2$ is —H, or is a (C$_{1-8}$)alkyl, (C$_{3-12}$)cycloalkyl, (C$_{6-10}$)aryl or (C$_{6-10}$)aryl(C$_{1-6}$)alkyl;

R$_3$ is —H or —F;

R$_4$ is —H, —F, —CF$_3$, —CF$_2$CF$_3$, —CF$_2$CF$_2$CF$_3$, —C(O)OR$_5$, or —C(O)NR$_5$R$_6$ or is a (C$_{1-8}$)alkyl, (C$_{3-12}$)cycloalkyl, (C$_{6-10}$)aryl or (C$_{6-10}$)aryl(C$_{1-6}$)alkyl;

R$_5$ and R$_6$ are each independently —H, or a C$_{1-8}$)alkyl, (C$_{3-12}$)cycloalkyl, (C$_{6-10}$)aryl or (C$_{6-10}$)aryl(C$_{1-6}$)alkyl;

P$_2$ is Ala, bAla, Leu, Ile, Val, Nva, bVal, Met, Nle, Gly, Phe, Tyr, or Nal(1) where the nitrogen of the alpha-amino group is optionally substituted with an R group where R is a (C$_{1-8}$)alkyl, (C$_{3-12}$)cycloalkyl, (C$_{3-12}$)cycloalkyl(C$_{1-6}$)alkyl, (C$_{4-11}$)bicycloalkyl, (C$_{4-11}$)bicycloalkyl(C$_{1-6}$)alkyl, (C$_{6-10}$)aryl, (C$_{6-10}$)aryl(C$_{1-6}$)alkyl, fused (C$_{6-10}$)aryl(C$_{3-12}$)cycloalkyl, fused (C$_{6-10}$)aryl(C$_{3-12}$)cycloalkyl(C$_{1-6}$)alkyl, or P$_2$ is Pro;

P$_3$ is Ala, bAla, Leu, Ile, Val, Nva, bVal, Met, or Nle or an N-methyl derivative, Pro or Lys substituted on its epsilon amino group with a morpholino-B-group or Orn substituted on its delta amino group with a morpholino-B-group;

P$_4$ is a bond;

K is hydrogen, formyl, acetyl, succinyl, benzoyl, t-butyloxycarbonyl, carbobenzyloxy, tosyl, dansyl, isovaleryl, methoxysuccinyl, 1-adamantanesulphonyl, 1-adamantaneacetyl, 2-carboxybenzoyl, phenylacetyl, t-butylacetyl, bis((1-naphthyl)methyl)acetyl, —C(O)N—(CH$_3$)$_2$, or -A-R$_z$ wherein

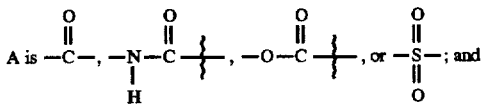

R$_z$ is an aryl group containing 6, 10 or 12 carbons substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino wherein the alkyl group contains 1 to 6 carbons, or K is

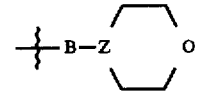

wherein

Z is N, and

B is a group of the formulae

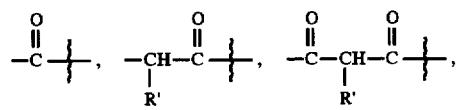

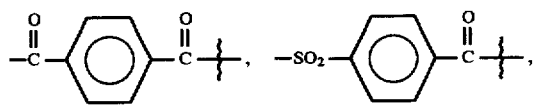

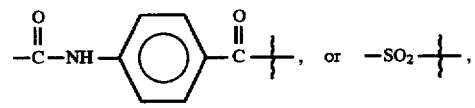

and wherein R' is hydrogen or a (C$_{1-6}$)alkyl group; or a hydrate, isostere or pharmaceutically acceptable salt thereof.

2. A compound of claim 1 wherein

R$_1$ is —CH(CH$_3$)$_2$ or —CH$_2$CH$_2$CH$_3$;

R$_2$ is —H, (C$_{1-8}$)alkyl, (C$_{3-12}$)cycloalkyl or (C$_{6-10}$)aryl;

R$_3$ is —F;

R$_4$ is —H, —F, —CF$_3$, —C(O)OR$_5$, —C(O)NR$_5$R$_6$, (C$_{1-8}$)alkyl, cyclopentyl, cyclohexyl, phenyl, benzyl;

R$_5$ and R$_6$ are each independently —H, (C$_{1-8}$)alkyl, cyclopentyl, cyclohexyl, phenyl, or benzyl;

P$_2$ is Pro;

P₃ is Ile, Val or Ala;
P₄ is a bond;
K is benzoyl, t-butyloxycarbonyl, carbobenzyloxy, isovaleryl, —C(O)N(CH₃)₂, or

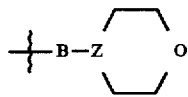

wherein
Z is N and
B is a group of the formulae

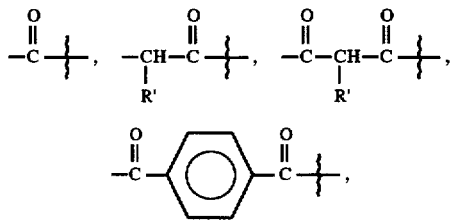

and wherein R' is hydrogen or a (C₁₋₆)alkyl group.

3. A compound of claim 2 wherein

R₂ is —H, methyl, ethyl, n-propyl, isopropyl, n-butyl, cyclopentyl, cyclohexyl, or phenyl;

R₄ is —H, —F, —CF₃, —C(O)OR₅, —C(O)NR₅R₆, methyl, ethyl, n-propyl, isopropyl, n-butyl, tert-butyl, cyclopentyl, cyclohexyl, phenyl, benzyl;

R₅ and R₆ are each independently —H, methyl, ethyl, n-propyl, isopropyl, n-butyl, tert-butyl, cyclopentyl, cyclohexyl, phenyl or benzyl.

4. A compound of claim 2 wherein
K is t-butyloxycarbonyl, or

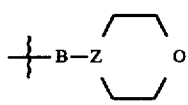

wherein
Z is N and
B is a group of the formulae

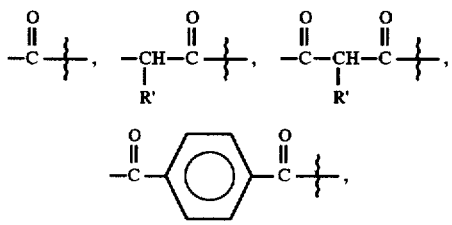

and wherein R' is isopropyl.

5. A compound of claim 4 wherein

R₂ is —H, methyl, ethyl, n-propyl, isopropyl, n-butyl, cyclopentyl, cyclohexyl, or phenyl;

R₄ is —H, —F, —CF₃, —C(O)OR₅, —C(O)NR₅R₆, methyl, ethyl, n-propyl, isopropyl, n-butyl, tert-butyl, cyclopentyl, cyclohexyl, phenyl, benzyl;

R₅ and R₆ are each independently —H, methyl, ethyl, n-propyl, isopropyl, n-butyl, tert-butyl, cyclopentyl, cyclohexyl, phenyl or benzyl.

6. A compound of claim 1 wherein

R₁ is —CH(CH₃)₂;

R₂ is —H, methyl, ethyl, n-propyl, isopropyl, n-butyl, cyclopentyl, cyclohexyl, or phenyl;

R₃ is —F;

R₄ is —F or —CF₃;

P₂ is Pro;

P₃ is Ile, Val or Ala;

P₄ is a bond;

K is

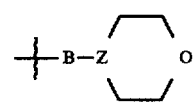

wherein
Z is N and
B is a group of the formulae

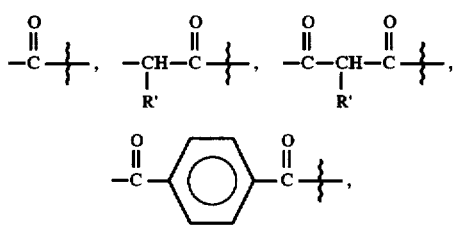

and wherein R' is isopropyl.

7. A compound of claim 1 wherein EAC is

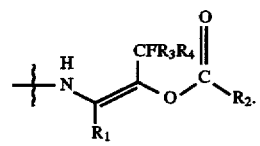

8. A compound of claim 2 wherein EAC is

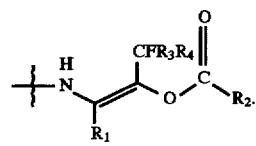

9. A compound of claim 3 wherein EAC is

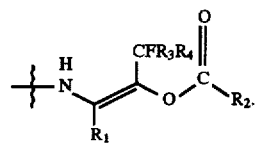

10. A compound of claim 4 wherein EAC is

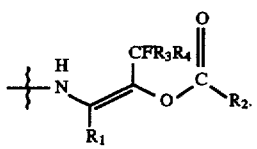

11. A compound of claim 5 wherein EAC is

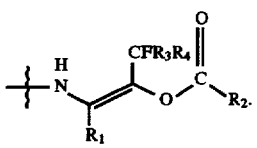

12. A compound of claim 6 wherein EAC is

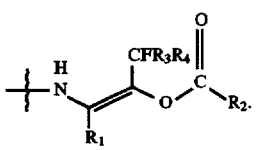

13. A compound of claim 1 wherein said compound is (E)-N-[4-(4-morpholinylcarbonyl)benzoyl]-L-valyl-N-[2-(acetyloxy)-3,3,4,4,4-pentafluoro-1-(1-methylethyl)-1-butenyl]-L-prolinamide.

14. A compound of claim 1 wherein said compound is (E)-N-[4-(4-morpholinylcarbonyl)benzoyl]-L-valyl-N-[3,3,4,4,4-pentafluoro-1-(1-methylethyl)-2-(1-oxopropoxy)-1-butenyl]-L-prolinamide.

15. A compound of claim 1 wherein said compound is (E)-N-[4-(4-morpholinylcarbonyl)benzoyl]-L-valyl-N-[3,4,4,4-pentafluoro-1-(1-methylethyl)-2-(2-methyl-1-oxopropoxy)-1-butenyl]-L-prolinamide.

16. A compound of claim 1 wherein said compound is (Z)-N-[4-(4-morpholinylcarbonyl)benzoyl]-L-valyl-N-[2-(acetyloxy)-3,3,4,4,4-pentafluoro-1-(1-methylethyl)-1-butenyl]-L-prolinamide.

17. A compound of claim 1 wherein said compound is (E)-N-[4-(4-morpholinylcarbonyl)benzoyl]-L-valyl-N-[2-(acetyloxy)-3,3,3-trifluoro-1-(1-methylethyl)-1-propenyl]-L-prolinamide.

18. A compound of claim 1 wherein said compound is (E)-N-(4-morpholinylcarbonyl)-L-valyl-N-[2-(acetyloxy)-3,3,3-trifluoro-t-(1-methylethyl)-1-propenyl]-L-prolinamide.

19. A pharmaceutical composition comprising a compound of claim 1 and a pharmaceutically acceptable carrier.

20. A method of treating a neutrophil associated inflammatory disease in a patient in need thereof which comprises administering to the patient an anti-inflammatory effective amount of a compound of claim 1.

21. A method of treating emphysema in a patient in need thereof which comprises administering to the patient an anti-inflammatory effective amount of a compound of claim 1.

22. A method of treating cystic fibrosis in a patient in need thereof which comprises administering to the patient an anti-inflammatory effective amount of a compound of claim 1.

23. A method of treating chronic bronchitis in a patient in need thereof which comprises administering to the patient an anti-inflammatory effective amount of a compound of claim 1.

24. A method of treating inflammatory bowel disease in a patient in need thereof which comprises administering to the patient an anti-inflammatory effective amount of a compound of claim 1.

* * * * *

UNITED STATES PATENT AND TRADEMARK OFFICE
CERTIFICATE OF CORRECTION

PATENT NO. : 5,698,523

DATED : December 16, 1997

INVENTOR(s) : Norton P. Peet, et al.

It is certified that error appears in the above-identified patent and that said Letters Patent is hereby corrected as shown below:

At column 13, line 46, "carboxbenzoyl" should read --carboxybenzoyl--.
At column 22, line 5, the patent reads "Sheme" and should read --Scheme--.
At column 23, line 13, the patent reads "of one" and should read --by one of--.
At column 29, line 33, the patent reads "(br s, 2E)" and should read --(br s, 2H)--.
At column 36, line 6, the patent reads "chromatograpy" and should read --chromatography--.
At column 39, line 42, the patent reads "weiging" and should read --weighing--.
At column 41, line 5, the patent reads "rspiratory" and should read --respiratory--.
At column 42, line 57, the patent reads "aerosol are" and should read --aerosol is--.
At column 55, line 35, claim 15, the patent reads "[3,4,4,4" and should read --[3,3,4,4,4-- .
At column 56, line 11, the patent reads "trifluoro-+-" and should read --trifluoro-1- --.

Signed and Sealed this

Twenty-ninth Day of December, 1998

Attest:

BRUCE LEHMAN

Attesting Officer   Commissioner of Patents and Trademarks